US012725249B2

(12) United States Patent
Peleg

(10) Patent No.: US 12,725,249 B2
(45) Date of Patent: Sep. 1, 2026

(54) SYSTEMS AND METHODS FOR IDENTIFYING IMAGES OF POLYPS

(71) Applicant: Given Imaging LTD., Yoqneam (IL)

(72) Inventor: Dori Peleg, Kiryat Bialik (IL)

(73) Assignee: GIVEN IMAGING LTD., Yoqneam (IL)

( * ) Notice: Subject to any disclaimer, the term of this patent is extended or adjusted under 35 U.S.C. 154(b) by 580 days.

(21) Appl. No.: 18/020,291

(22) PCT Filed: Sep. 3, 2021

(86) PCT No.: PCT/IL2021/051083
§ 371 (c)(1),
(2) Date: Feb. 8, 2023

(87) PCT Pub. No.: WO2022/054046
PCT Pub. Date: Mar. 17, 2022

(65) Prior Publication Data

US 2023/0274422 A1 Aug. 31, 2023

Related U.S. Application Data

(60) Provisional application No. 63/075,795, filed on Sep. 8, 2020.

(51) Int. Cl.
*G06T 7/00* (2017.01)
*A61B 1/04* (2006.01)
(Continued)

(52) U.S. Cl.
CPC ........... *G06T 7/0012* (2013.01); *G16H 30/40* (2018.01); *G16H 50/20* (2018.01); *A61B 1/041* (2013.01);
(Continued)

(58) Field of Classification Search
CPC ......... G06T 7/0012; G06T 2207/10016; G06T 2207/10068; G06T 2207/20081;
(Continued)

(56) References Cited

U.S. PATENT DOCUMENTS 9,430,706 B1 8/2016 Peleg
2010/0303322 A1* 12/2010 Whelan ................ G06T 7/0012 382/131
(Continued)

FOREIGN PATENT DOCUMENTS

JP 2005198970 A 7/2005
JP 2022505154 A 1/2022
(Continued)

OTHER PUBLICATIONS

Peleg, Dori, “Big Data-Small Data: Image Classification for Colorectal Cancer Diagnosis”, Mar. 28, 2017 (Mar. 28, 2017), Retrieved from the Internet on Mar. 18, 2022: URL:https://www.imvc.co.il/Portals/38/Peleg%20Dori.pdf.
(Continued)

*Primary Examiner* — Jennifer Mehmood
*Assistant Examiner* — Jose M Torres
(74) *Attorney, Agent, or Firm* — Carter, DeLuca & Farrell, LLP

(57) ABSTRACT

Systems and methods are disclosed for identifying images that contain polyps. An exemplary method for identifying images includes: accessing images of a gastrointestinal tract (GIT) captured by a capsule endoscopy device, where: each image of the images is suspected to include a polyp and is associated with a probability of containing the polyp, and the images include seed images, where each seed image is associated with one or more images of the images. The image(s) associated with each seed image is identified as suspected to include the same polyp as the associated seed
(Continued)

image. The method includes applying a polyp detection system on the seed images to identify seed images which include polyps, where the polyp detection system is applied to each seed image of based on the image(s) associated with the seed image and the probabilities associated with the seed image and with the associated image(s).

16 Claims, 17 Drawing Sheets

(51) Int. Cl.
*G16H 30/40* (2018.01)
*G16H 50/20* (2018.01)

(52) U.S. Cl.
CPC ............... *G06T 2207/10016* (2013.01); *G06T 2207/10068* (2013.01); *G06T 2207/20081* (2013.01); *G06T 2207/30032* (2013.01); *G06T 2207/30092* (2013.01); *G06T 2207/30096* (2013.01)

(58) Field of Classification Search
CPC . G06T 2207/30032; G06T 2207/30092; G06T 2207/30096; G16H 30/40; G16H 50/20; A61B 1/041
See application file for complete search history.

(56) References Cited

U.S. PATENT DOCUMENTS

| | | | | |
|---|---|---|---|---|
| 2018/0225820 | A1* | 8/2018 | Liang | G06V 10/82 |
| 2018/0253839 | A1* | 9/2018 | Zur | A61B 1/000094 |
| 2020/0143936 | A1 | 5/2020 | Kamon et al. | |
| 2021/0133964 | A1* | 5/2021 | Sachdev | G06T 5/77 |
| 2021/0366593 | A1* | 11/2021 | Takenouchi | G06T 11/00 |

FOREIGN PATENT DOCUMENTS

| | | | |
|---|---|---|---|
| WO | 2017199258 | A1 | 11/2017 |
| WO | 2020079696 | A1 | 4/2020 |
| WO | 2020105699 | A1 | 5/2020 |

OTHER PUBLICATIONS

International Search Report and Written Opinion of the International Searching Authority issued in corresponding application PCT/IL2021/051083 mailed Apr. 29, 2022 (17 pages).

Office Action for Japanese Application No. 2023-515284 dated Aug. 22, 2025 with English translation, 8 pages.

Chinese Office Action for Application No. 202180070844.1 dated Dec. 25, 2025 with English translation, 10 pages.

Extended European Search Report for Application No. 25204405.2 dated Jan. 9, 2026, 13 pages.

* cited by examiner

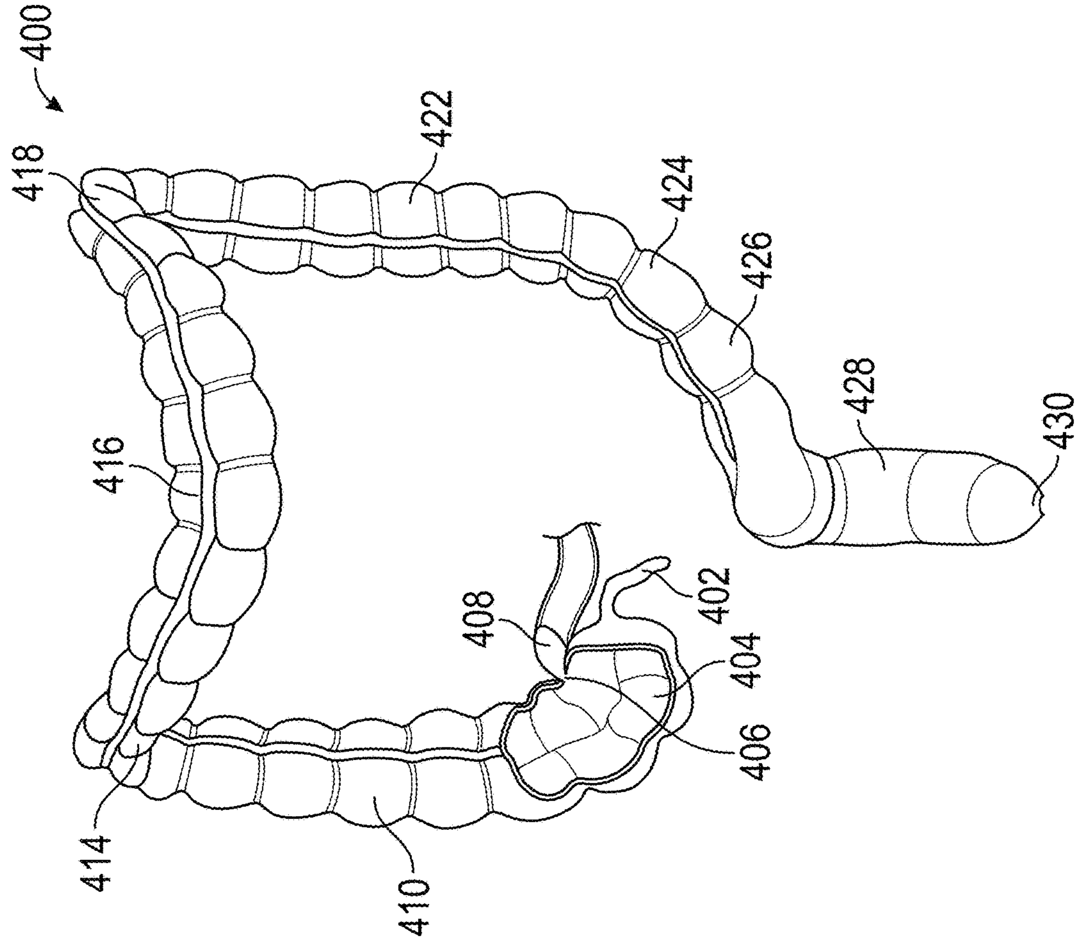
FIG. 4
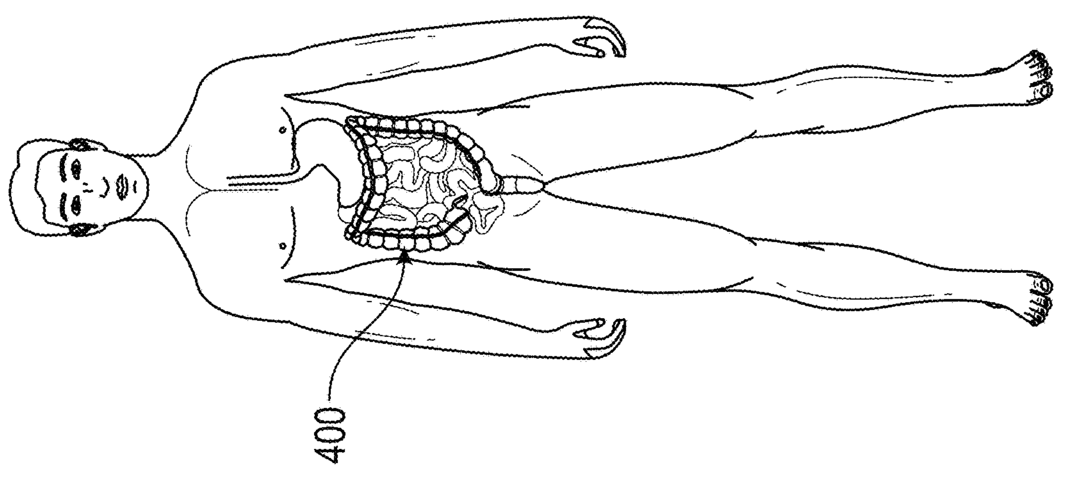

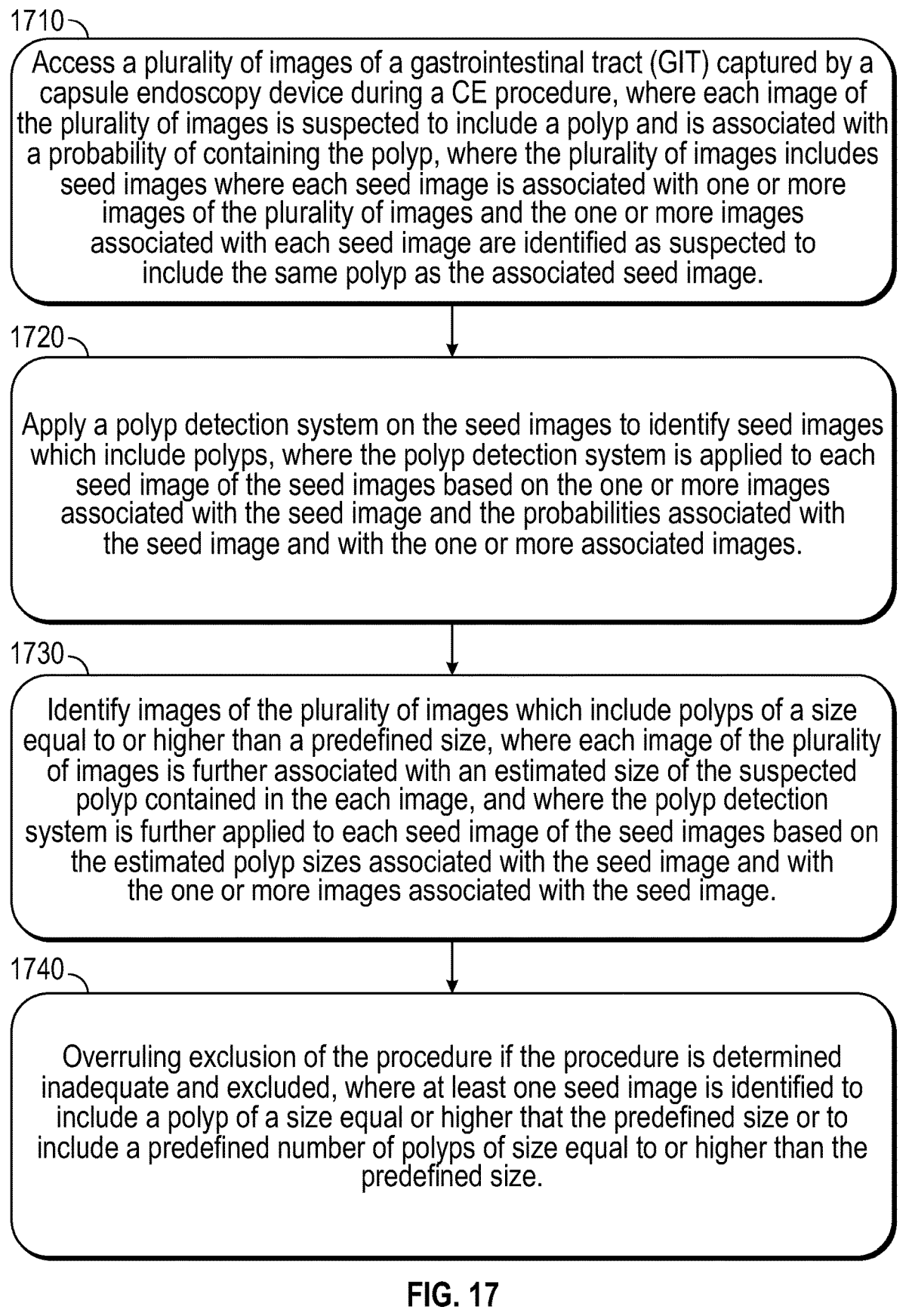

1710

Access a plurality of images of a gastrointestinal tract (GIT) captured by a capsule endoscopy device during a CE procedure, where each image of the plurality of images is suspected to include a polyp and is associated with a probability of containing the polyp, where the plurality of images includes seed images where each seed image is associated with one or more images of the plurality of images and the one or more images associated with each seed image are identified as suspected to include the same polyp as the associated seed image.

1720

Apply a polyp detection system on the seed images to identify seed images which include polyps, where the polyp detection system is applied to each seed image of the seed images based on the one or more images associated with the seed image and the probabilities associated with the seed image and with the one or more associated images.

1730

Identify images of the plurality of images which include polyps of a size equal to or higher than a predefined size, where each image of the plurality of images is further associated with an estimated size of the suspected polyp contained in the each image, and where the polyp detection system is further applied to each seed image of the seed images based on the estimated polyp sizes associated with the seed image and with the one or more images associated with the seed image.

1740

Overruling exclusion of the procedure if the procedure is determined inadequate and excluded, where at least one seed image is identified to include a polyp of a size equal or higher that the predefined size or to include a predefined number of polyps of size equal to or higher than the predefined size.

FIG. 17

SYSTEMS AND METHODS FOR IDENTIFYING IMAGES OF POLYPS

CROSS-REFERENCE TO RELATED APPLICATION

The present application is a U.S. National Stage Application filed under 35 U.S.C. § 371(a) of International Patent Application No. PCT/IL2021/051083, filed Sep. 3, 2021, which claims the benefit of and priority to U.S. Provisional Application No. 63/075,795, filed Sep. 8, 2020. The entire contents of each of the foregoing applications are hereby incorporated by reference.

FIELD

The disclosure relates to image analysis of in-vivo images of a gastrointestinal tract (GIT) and, more particularly, to systems and methods for identifying images of polyps in a GIT.

BACKGROUND

Capsule endoscopy (CE) allows examining the entire GIT endoscopically. There are capsule endoscopy systems and methods that are aimed at examining a specific portion of the GIT, such as the small bowel (SB) or the colon. CE is a non-invasive procedure which does not require the patient to be admitted to a hospital, and the patient can continue most daily activities while the capsule is in his body.

On a typical CE procedure, the patient is referred to a procedure by a physician. The patient then arrives at a medical facility (e.g., a clinic or a hospital), to perform the procedure. The capsule, which is about the size of a multi-vitamin, is swallowed by the patient under the supervision of a health professional (e.g., a nurse or a physician) at the medical facility and the patient is provided with a wearable device, e.g., a sensor belt and a recorder placed in a pouch and strap to be placed around the patient's shoulder. The wearable device typically includes a storage device. The patient may be given guidance and/or instructions and then released to his daily activities.

The capsule captures images as it travels naturally through the GIT. Images and additional data (e.g., metadata) are then transmitted to the recorder that is worn by the patient. The capsule is typically disposable and passes naturally with a bowel movement. The procedure data (e.g., the captured images or a portion of them and additional metadata) is stored on the storage device of the wearable device.

The wearable device is typically returned by the patient to the medical facility with the procedure data stored thereon. The procedure data is then downloaded to a computing device typically located at the medical facility, which has an engine software stored thereon. The received procedure data is then processed by the engine to a compiled study (or "study"). Typically, a study includes thousands of images (around 6,000). Typically, the number of images to be processed is of the order of tens of thousands and about 90,000 on average.

A reader (which may be the procedure supervising physician, a dedicated physician or the referring physician) may access the study via a reader application. The reader then reviews the study, evaluates the procedure and provides his input via the reader application. Since the reader needs to review thousands of images, the reading time of a study may usually take between half an hour to an hour on average and the reading task may be tiresome. A report is then generated by the reader application based on the compiled study and the reader's input. On average, it would take an hour to generate a report. The report may include, for example, images of interest, e.g., images which are identified as including pathologies, selected by the reader; evaluation or diagnosis of the patient's medical condition based on the procedure's data (i.e., the study) and/or recommendations for follow up and/or treatment provided by the reader. The report may be then forwarded to the referring physician. The referring physician may decide on a required follow up or treatment based on the report.

SUMMARY

To the extent consistent, any or all of the aspects detailed herein may be used in conjunction with any or all of the other aspects detailed herein. Aspects of the present disclosure relate to identifying images of polyps with a high degree of confidence. Due to the high degree of confidence, aspects of the present disclosure relate to using the identified images in automated ways without prompting or intervention by a human, and/or relate to presenting the identified images to a health professional when such images may have been missed during a human review, and/or relate to overriding the decisions of other tools which may have incorrectly designated the identified images.

In accordance with aspects of the present disclosure, a method for identifying images including polyps includes: accessing a plurality of images of a gastrointestinal tract (GIT) captured by a capsule endoscopy device during a CE procedure, where: each image of the plurality of images is suspected to include a polyp and associated with a probability of containing the polyp, and the plurality of images includes seed images and each seed image is associated with one or more images of the plurality of images, where the one or more images are associated with each seed image identified as suspected to include the same polyp as the associated seed image; and applying a polyp detection system on the seed images to identify seed images which include polyps, where the polyp detection system is applied to each seed image of the seed images based on the one or more images associated with the seed image and the probabilities associated with the seed image and with the one or more associated images.

In various embodiments of the method, the method includes identifying images of the plurality of images which include polyps of a size equal to or higher than a predefined size, where each image of the plurality of images is further associated with an estimated size of the suspected polyp contained in the each image, and where the polyp detection system is further applied to each seed image of the seed images based on the estimated polyp size associated with the seed image and with the one or more images associated with the seed image.

In various embodiments of the method, the procedure is determined inadequate and excluded, and at least one seed image is identified to include a polyp of a size equal or higher that the predefined size or to include a predefined number of polyps of a size equal to or higher than the predefined size, and the method includes overruling the exclusion of the procedure.

In various embodiments of the method, the polyp detection system includes at least one of: one or more positive filters, one or more negative filters, one or more classical machine learning systems, or a combination thereof.

In various embodiments of the method, the method inputs to the one or more classical machine learning systems, the one or more positive filters or the one or more negative filters include at least one of: a seed image probability of containing a polyp, number of images associated with a seed image, number of images associated with a seed image having a probability of containing a polyp according to a predefined threshold, or a combination thereof.

In various embodiments of the method, the one or more images associated with each seed image are determined by applying a tracker which tracks the suspected polyp contained in each seed image in adjacent images, or by using a classification system which compares the seed image with adjacent images.

In various embodiments of the method, the method the accessed plurality of images of the gastrointestinal tract (GIT) are images of a CE procedure study.

In various embodiments of the method, the method includes selecting the seed images from the plurality of images.

In various embodiments of the method, the method includes providing an indication to a CE procedure referring physician to refer a CE procedure subject to a colonoscopy procedure based on the seed images identified to include polyps.

In various embodiments of the method, the method includes, for each image of the plurality of images: applying a classical machine learning system configured to provide the probability of the image containing the polyp, based on input features corresponding to the image, and accessing a soft margin of the classical machine learning system corresponding to the image; and determining, without human intervention, whether to recommend a colonoscopy based on the soft margins of the plurality of images.

In various embodiments of the method, the method includes accessing a mapping of soft margins to probabilities of an image containing a polyp, where the determining of whether to recommend a colonoscopy is further based on the mapping of soft margins to probabilities of an image containing a polyp.

In various embodiments of the method, the method includes, for each image of the plurality of images, accessing an estimated polyp size for the image, the estimated polyp size generated based on the image; and accessing a mapping of estimated polyp sizes to probabilities of an actual polyp size being at least a predefined size, where the determining of whether to recommend a colonoscopy is further based on the estimated polyp sizes and the mapping of estimated polyp sizes to probabilities of an actual polyp size being at least a predefined size.

In various embodiments of the method, the method includes displaying the seed images identified to include polyps.

In various embodiments of the method, the method includes providing a therapeutic recommendation based on the seed images identified to include polyps.

In various embodiments of the method, the method includes displaying the seed images and indicating the seed images identified to include polyps.

In various embodiments of the method, the method includes: displaying at least the seed images to a user; receiving user selections of images among the displayed images; determining at least one unselected image which was not selected by a user and which is among the seed images identified to include polyps; and presenting the at least one unselected image to the user.

In various embodiments of the method, the method the images selected by the user are images selected to be included in the CE procedure report.

In various embodiments of the method, the method the presenting of the at least one unselected image to the user is performed once a request to generate a report is received.

In accordance with aspects of the present disclosure, a method for identifying images includes accessing a plurality of images of a gastrointestinal tract (GIT) captured by a capsule endoscopy device where the plurality of images has a likelihood of containing a polyp, applying at least one filter to the plurality of images where the at least one filter includes at least one of: a positive filter configured to identify images to designate as containing a polyp or a negative filter configured to identify images to not designate as containing a polyp, and providing information based on at least one of: at least one image of the plurality of images which was identified by the at least one filter, or at least one image of the plurality of images which was not identified by the at least one filter.

In various embodiments of the method, the negative filter is configured to identify images to not designate as containing a polyp based on the images being images of a body exit portion of the GIT.

In various embodiments of the method, the negative filter is configured to identify images to not designate as containing a polyp based on the images being evaluated to be images of at least one of an ileocecal valve or a hemorrhoidal plexus.

In various embodiments of the method, the negative filter is configured to identify images to not designate as containing a polyp based on the images being evaluated to contain a polyp for which an estimated polyp size is below a threshold size.

In various embodiments of the method, the method further includes, for each image of the plurality of images, accessing a track of images for the image.

In various embodiments of the method, the negative filter is configured to identify images to not designate as containing a polyp based on the track of images for an image having only one image with a polyp presence probability above a threshold value.

In various embodiments of the method, the positive filter is configured to identify images to designate as containing a polyp based on the tracks of images.

In various embodiments of the method, the positive filter is configured to identify images to designate as containing a polyp based on the track of images for an image having at least a threshold number of images with a polyp presence probability above a threshold value.

In accordance with aspects of the present disclosure, a system for identifying images includes one or more processors and at least one memory storing instructions. The instructions, when executed by the one or more processors, cause the system to access a plurality of images of a gastrointestinal tract (GIT) captured by a capsule endoscopy device where the plurality of images has a likelihood of containing a polyp, apply at least one filter to the plurality of images where the at least one filter includes at least one of: a positive filter configured to identify images to designate as containing a polyp or a negative filter configured to identify images to not designate as containing a polyp, and provide information based on at least one of: at least one image of the plurality of images which was identified by the at least one filter, or at least one image of the plurality of images which was not identified by the at least one filter.

In various embodiments of the system, the negative filter is configured to identify images to not designate as containing a polyp based on the images being images of a body exit portion of the GIT.

In various embodiments of the system, the negative filter is configured to identify images to not designate as containing a polyp based on the images being evaluated to be images of at least one of an ileocecal valve or a hemorrhoidal plexus.

In various embodiments of the system, the negative filter is configured to identify images to not designate as containing a polyp based on the images being evaluated to contain a polyp for which an estimated polyp size is below a threshold size.

In various embodiments of the system, the instructions, when executed by the one or more processors, further cause the system to, for each image of the plurality of images, access a track of images for the image.

In various embodiments of the system, the negative filter is configured to identify images to not designate as containing a polyp based on the track of images for an image having only one image with a polyp presence probability above a threshold value.

In various embodiments of the system, the positive filter is configured to identify images to designate as containing a polyp based on the tracks of images.

In various embodiments of the system, the positive filter is configured to identify images to designate as containing a polyp based on the track of images for an image having at least a threshold number of images with a polyp presence probability above a threshold value.

In accordance with aspects of the present disclosure, a method for identifying images includes accessing a plurality of images of a gastrointestinal tract (GIT) captured by a capsule endoscopy device where the plurality of images has a likelihood of containing a polyp; for each image of the plurality of images: applying a classical machine learning system configured to provide an indication, based on input features corresponding to the image, of whether the image contains a polyp or does not contains a polyp; and presenting information based on at least one image of the plurality of images which has an indication, provided by the classical machine learning system of containing a polyp, which satisfies a confidence threshold.

In various embodiments of the method, the method further includes, for each image of the plurality of images: accessing a track of images for the image.

In various embodiments of the method, the input features corresponding to the image include at least one of: a track length of the track of images, or a number of images in the track of images which has a polyp presence score above a threshold value.

In various embodiments of the method, the input features corresponding to the image include an index difference between an index of the image and an index of an image of an ileocecal valve.

In various embodiments of the method, the input features corresponding to the image include a segment number of a colon segment in which the image was captured.

In various embodiments of the method, the classical machine learning classifier is a polynomial support vector machine.

In accordance with aspects of the present disclosure, a system for identifying images includes one or more processors and at least one memory storing instructions. The instructions, when executed by the one or more processors, cause the system to: access a plurality of images of a gastrointestinal tract (GIT) captured by a capsule endoscopy device where the plurality of images has a likelihood of containing a polyp; for each image of the plurality of images: apply a classical machine learning system configured to provide an indication, based on input features corresponding to the image, of whether the image contains a polyp or does not contains a polyp; and present information based on at least one image of the plurality of images which has an indication, provided by the classical machine learning system of containing a polyp, which satisfies a confidence threshold.

In various embodiments of the system, the instructions, when executed by the one or more processors, further cause the system to, for each image of the plurality of images, access a track of images for the image.

In various embodiments of the system, the input features corresponding to the image include at least one of: a track length of the track of images, or a number of images in the track of images which has a polyp presence score above a threshold value.

In various embodiments of the system, the input features corresponding to the image include an index difference between an index of the image and an index of an image of an ileocecal valve.

In various embodiments of the system, the input features corresponding to the image include a segment number of a colon segment in which the image was captured.

In various embodiments of the system, the classical machine learning classifier is a polynomial support vector machine.

In accordance with aspects of the present disclosure, a method for identifying images includes: accessing a plurality of images of a gastrointestinal tract (GIT) captured by a capsule endoscopy device where the plurality of images has a likelihood of containing a polyp; applying at least one filter to the plurality of images where the at least one filter includes at least one of: a positive filter configured to identify images to designate as containing a polyp or a negative filter configured to identify images to not designate as containing a polyp; providing at least one unfiltered image by selecting at least one image from the plurality of images which was not identified by the at least one filter; for each unfiltered image of the at least one unfiltered image: applying a classical machine learning system configured to provide an indication, based on input features corresponding to the unfiltered image, of whether the unfiltered image contains a polyp or does not contains a polyp; and presenting information based on at least one image of the at least one unfiltered image which has an indication, provided by the classical machine learning system of containing a polyp, which satisfies a confidence threshold.

In various embodiments of the method, the method further includes generating, without human intervention, a capsule endoscopy report to present to a clinician where the capsule endoscopy report includes at least one of: the at least one image of the at least one unfiltered image which has an indication, provided by the classical machine learning system of containing a polyp, which satisfies a confidence threshold, or at least one image which is identified by a positive filter.

In various embodiments of the method, the method further includes: receiving user selections of images among the plurality of images; determining at least one unselected image which was not selected by a user and which is among the at least one image of the at least one unfiltered image which has an indication, provided by the classical machine learning system of containing a polyp, which satisfies a confidence threshold; and presenting the at least one unselected image to the user.

In accordance with aspects of the present disclosure, a system for identifying images includes one or more processors and at least one memory storing instructions. The instructions, when executed by the one or more processors, cause the system to: access a plurality of images of a gastrointestinal tract (GIT) captured by a capsule endoscopy device where the plurality of images has a likelihood of containing a polyp; apply at least one filter to the plurality of images where the at least one filter includes at least one of: a positive filter configured to identify images to designate as containing a polyp or a negative filter configured to identify images to not designate as containing a polyp; provide at least one unfiltered image by selecting at least one image from the plurality of images which was not identified by the at least one filter; for each unfiltered image of the at least one unfiltered image: apply a classical machine learning system configured to provide an indication, based on input features corresponding to the unfiltered image, of whether the unfiltered image contains a polyp or does not contains a polyp; and present information based on at least one image of the at least one unfiltered image which has an indication, provided by the classical machine learning system of containing a polyp, which satisfies a confidence threshold.

In various embodiments of the system, the instructions, when executed by the one or more processors, further cause the system to: generate, without human intervention, a capsule endoscopy report to present to a clinician where the capsule endoscopy report includes at least one of: the at least one image of the at least one unfiltered image which has an indication, provided by the classical machine learning system of containing a polyp, which satisfies a confidence threshold, or at least one image which is identified by a positive filter.

In various embodiments of the system, the instructions, when executed by the one or more processors, further cause the system to: receive user selections of images among the plurality of images; determine at least one unselected image which was not selected by a user and which is among the at least one image of the at least one unfiltered image which has an indication, provided by the classical machine learning system of containing a polyp, which satisfies a confidence threshold; and present the at least one unselected image to the user.

In accordance with aspects of the present disclosure, a computer-implemented method for recommending a colonoscopy includes: accessing a plurality of images of a gastrointestinal tract (GIT) captured by a capsule endoscopy device where the plurality of images has a likelihood of containing a polyp; for each image of the plurality of images: applying a classical machine learning system configured to provide an indication, based on input features corresponding to the image, of whether the image contains a polyp or does not contains a polyp, and accessing a soft margin of the classical machine learning system corresponding to the image; and determining, without human intervention, whether to recommend a colonoscopy based on the soft margins of the plurality of images.

In various embodiments of the method, the method further includes accessing a mapping of soft margins to probabilities of an image containing a polyp, where the determining of whether to recommend a colonoscopy is further based on the mapping of soft margins to probabilities of an image containing a polyp.

In various embodiments of the method, the method further includes: for each image of the plurality of images, accessing an estimated polyp size for the image where the estimated polyp size is generated based on the image; and accessing a mapping of estimated polyp sizes to probabilities of an actual polyp size being at least a predefined in size, where the determining of whether to recommend a colonoscopy is further based on the estimated polyp sizes and the mapping of estimated polyp sizes to probabilities of an actual polyp size being at least a predefined in size.

In accordance with aspects of the present disclosure, a system for recommending a colonoscopy includes one or more processors and at least one memory storing instructions. The instructions, when executed by the one or more processors, cause the system to: access a plurality of images of a gastrointestinal tract (GIT) captured by a capsule endoscopy device where the plurality of images has a likelihood of containing a polyp; for each image of the plurality of images: apply a classical machine learning system configured to provide an indication, based on input features corresponding to the image, of whether the image contains a polyp or does not contains a polyp, and access a soft margin of the classical machine learning system corresponding to the image; and determine, without human intervention, whether to recommend a colonoscopy based on the soft margins of the plurality of images.

In various embodiments of the system, the instructions, when executed by the one or more processors, further cause the system to access a mapping of soft margins to probabilities of an image containing a polyp, where the determining of whether to recommend a colonoscopy is further based on the mapping of soft margins to probabilities of an image containing a polyp.

In various embodiments of the system, the instructions, when executed by the one or more processors, further cause the system to: for each image of the plurality of images, access an estimated polyp size for the image where the estimated polyp size is generated based on the image; and access a mapping of estimated polyp sizes to probabilities of an actual polyp size being at least a predefined in size, where the determining of whether to recommend a colonoscopy is further based on the estimated polyp sizes and the mapping of estimated polyp sizes to probabilities of an actual polyp size being at least a predefined in size.

BRIEF DESCRIPTION OF DRAWINGS

The above and other aspects and features of the disclosure will become more apparent in view of the following detailed description when taken in conjunction with the accompanying drawings wherein like reference numerals identify similar or identical elements.

FIG. 4 is a diagram illustrating a colon;

FIG. 17 is a block diagram of another exemplary operation for selecting colon images which contain a colon polyp with a high degree of confidence, in accordance with aspects of the present disclosure.

DETAILED DESCRIPTION

Figure 1:
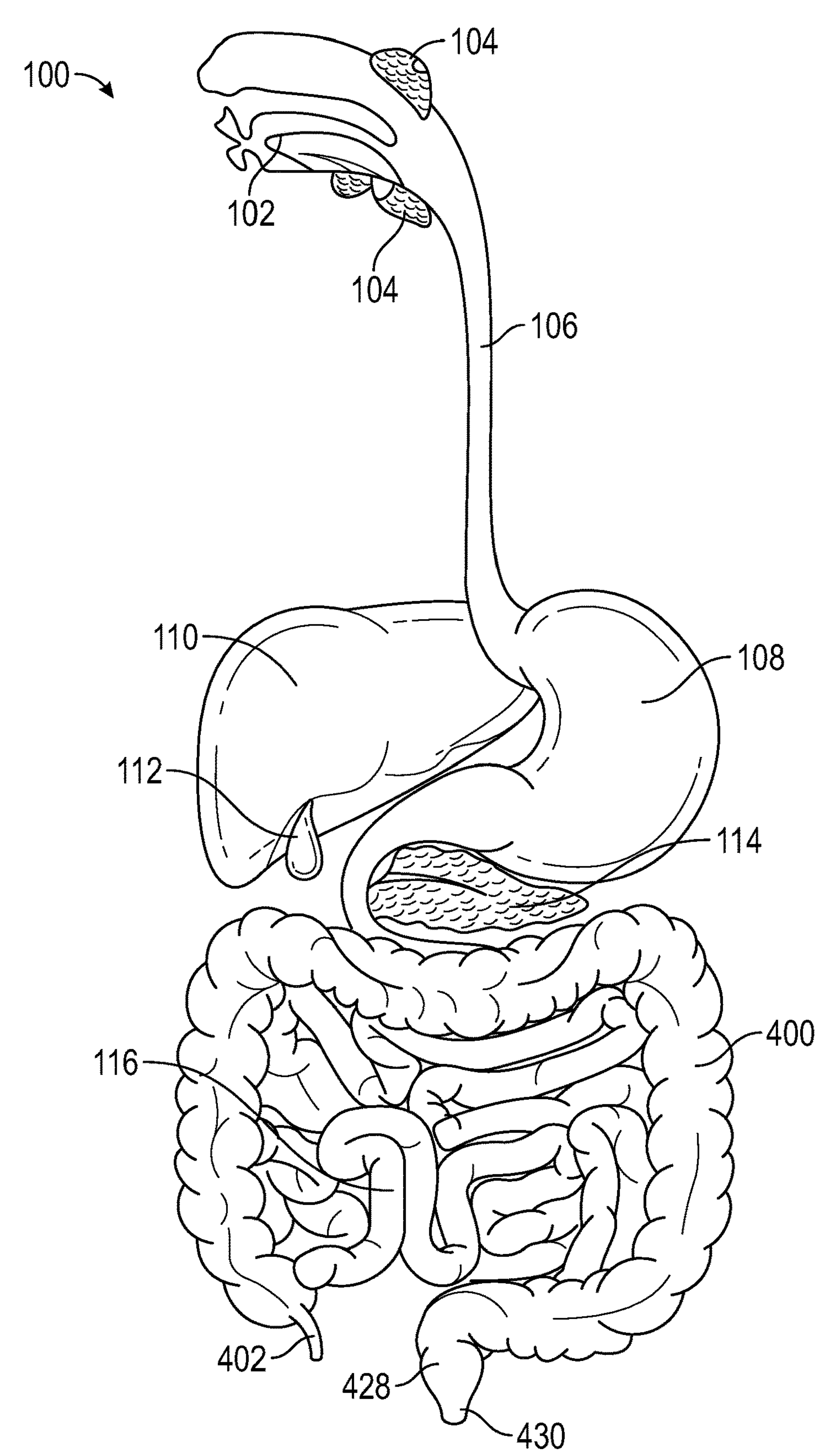
FIG. 1 is a diagram illustrating a gastrointestinal tract (GIT)

The present disclosure relates to systems and methods for identifying images of polyps, captured in vivo by a capsule endoscopy (CE) device, with a high degree of confidence. Due to the high degree of confidence, aspects of the present disclosure relate to using the identified images in automated ways without prompting or intervention by a human, and/or relate to presenting the identified images to a health professional when such images may have been missed during a human review, and/or relate to overriding the decisions of other tools which may have incorrectly designated the identified images. In various aspects, a decision for a subject image uses information of images related to the subject image, such as information of an image "track," which will be discussed in more detail later herein. In various aspects, a decision for a subject image uses weights such that not all images are considered equally. Aspects of the present disclosure involve deep learning machine learning in classification/detection to receive relatively high sensitivity and specificity, and aspects of the present disclosure use heuristics and/or "classical" machine learning (defined later) to optimize results and increase the sensitivity and/or specificity.

In the following detailed description, specific details are set forth in order to provide a thorough understanding of the disclosure. However, it will be understood by those skilled in the art that the disclosure may be practiced without these specific details. In other instances, well-known methods, procedures, and components have not been described in detail so as not to obscure the present disclosure. Some features or elements described with respect to one system may be combined with features or elements described with respect to other systems. For the sake of clarity, discussion of same or similar features or elements may not be repeated.

Although the disclosure is not limited in this regard, discussions utilizing terms such as, for example, "processing," "computing," "calculating," "determining," "establishing," "analyzing," "checking," or the like, may refer to operation(s) and/or process(es) of a computer, a computing platform, a computing system, or other electronic computing device, that manipulates and/or transforms data represented as physical (e.g., electronic) quantities within the computer's registers and/or memories into other data similarly represented as physical quantities within the computer's registers and/or memories or other information non-transitory storage medium that may store instructions to perform operations and/or processes. Although the disclosure is not limited in this regard, the terms "plurality" and "a plurality" as used herein may include, for example, "multiple" or "two or more". The terms "plurality" or "a plurality" may be used throughout the specification to describe two or more components, devices, elements, units, parameters, or the like. The term set when used herein may include one or more items. Unless explicitly stated, the methods described herein are not constrained to a particular order or sequence. Additionally, some of the described methods or elements thereof can occur or be performed simultaneously, at the same point in time, or concurrently.

The term "location" and its derivatives, as referred to herein with respect to an image, may refer to the estimated location of the capsule along the GIT (e.g., colon) while capturing the image or to the estimated location of the portion of the GIT shown in the image along the GIT.

A type of CE procedure may be determined based on, inter alia, the portion of the GIT that is of interest and is to be imaged (e.g., the colon), or based on the specific use (e.g., for checking the status of a GI disease, such as Crohn's disease, or for colon cancer screening).

The terms screen(s), view(s) and display(s) may be used herein interchangeably and may be understood according to the specific context.

The terms "surrounding" or "adjacent" as referred to herein with respect to images (e.g., images that surround another image(s), or that are adjacent to other image(s)), may relate to spatial and/or temporal characteristics unless specifically indicated otherwise. For example, images that surround or are adjacent to other image(s) may be images that are estimated to be located near the other image(s) along the GIT and/or images that were captured near the capture time of another image, within a certain threshold, e.g., within one or two centimeters, or within one, five, or ten seconds.

The terms "GIT" and "a portion of the GIT" may each refer to or include the other, according to their context. Thus, the term "a portion of the GIT" may also refer to the entire GIT and the term "GIT" may also refer only to a portion of the GIT.

The terms "image" and "frame" may each refer to or include the other and may be used interchangeably in the present disclosure to refer to a single capture by an imaging device. For convenience, the term "image" may be used more frequently in the present disclosure, but it will be understood that references to an image shall apply to a frame as well.

The term "classical machine learning" refers to machine learning which involves feature selection or feature engineering for the inputs of the machine learning.

The term "soft margin" may refer to the continuous output of a classifier (e.g., a classical machine learning algorithm) which is related to the distance between an example and a separating hyperplane/classification border of the classifier. A soft margin can be used to assess how sure the classifier is in its decision. The higher the absolute value of the soft margin, the farther from the classification border and the surer it is in its decision. The term "hard margin" may refer to the classification decision which results from applying a threshold (e.g., zero) on the soft margin and deciding to which class each example belongs.

The term "clinician" may refer to any healthcare provider or practitioner, including any physician, such as a gastroenterologist, primary care physician, or a referring physician.

Referring to FIG. 1, an illustration of the GIT 100 is shown. The GIT 100 is an organ system within humans and other animals. The GIT 100 generally includes a mouth 102 for taking in sustenance, salivary glands 104 for producing saliva, an esophagus 106 through which food passes aided by contractions, a stomach 108 to secret enzymes and stomach acid to aid in digesting food, a liver 110, a gall bladder 112, a pancreas 114, a small intestine/small bowel 116 ("SB") for the absorption of nutrients, and a colon 400 (e.g., large intestine) for storing water and waste material as feces prior to defecation. The colon 400 generally includes an appendix 402, a rectum 428, and an anus 430. Food taken in through the mouth is digested by the GIT to take in nutrients and the remaining waste is expelled as feces through the anus 430.

Studies of different portions of the GIT 100 (e.g., colon 400, esophagus 106, and/or stomach 108) may be presented via a suitable user interface. As used herein, the term "study" refers to and includes at least a set of images selected from the images captured by a CE imaging device (e.g., 212, FIG. 2) during a single CE procedure performed with respect to a specific patient and at a specific time, and can optionally include information other than images as well. The type of procedure performed may determine which portion of the GIT 100 is the portion of interest. Examples of types of procedures performed include, without limitation, a small bowel procedure, a colon procedure, a small bowel and colon procedure, a procedure aimed to specifically exhibit or check the small bowel, a procedure aimed to specifically exhibit or check the colon, a procedure aimed to specifically exhibit or check the colon and the small bowel, or a procedure to exhibit or check the entire GIT: esophagus, stomach, SB and colon.

Figure 2:
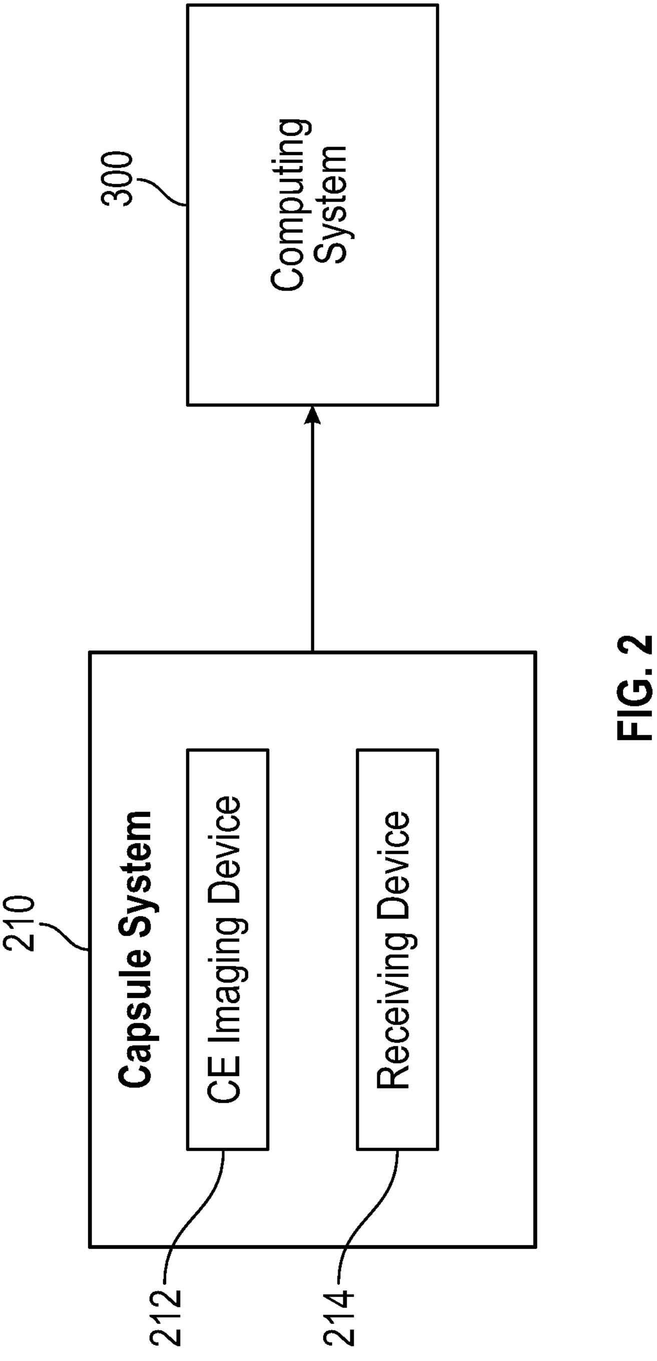
FIG. 2 is a block diagram of an exemplary system for analyzing medical images captured in vivo via a Capsule Endoscopy (CE) procedure, in accordance with aspects of the disclosure.

FIG. 2 shows a block diagram of a system for analyzing medical images captured in vivo via a CE procedure. The system generally includes a capsule system 210 configured to capture images of the GIT and a computing system 300 (e.g., local system and/or cloud system) configured to process the captured images.

The capsule system 210 may include a swallowable CE imaging device 212 (e.g., a capsule) configured to capture images of the GIT as the CE imaging device 212 travels through the GIT. The images may be stored on the CE imaging device 212 and/or transmitted to a receiving device 214 typically including an antenna. In some capsule systems 210, the receiving device 214 may be located on the patient who swallowed the CE imaging device 212 and may, for example, take the form of a belt worn by the patient or a patch secured to the patient.

The capsule system 210 may be communicatively coupled with the computing system 300 and can communicate captured images to the computing system 300. The computing system 300 may process the received images using image processing technologies, machine learning technologies, and/or signal processing technologies, among other technologies. The computing system 300 can include local computing devices that are local to the patient and/or the patient's treatment facility, a cloud computing platform that is provided by cloud services, or a combination of local computing devices and a cloud computing platform.

In the case where the computing system 300 includes a cloud computing platform, the images captured by the capsule system 210 may be transmitted online to the cloud computing platform. In various embodiments, the images can be transmitted via the receiving device 214 worn or carried by the patient. In various embodiments, the images can be transmitted via the patient's smartphone or via any other device connected to the Internet and which may be coupled with the CE imaging device 212 or the receiving device 214.

Figure 3:
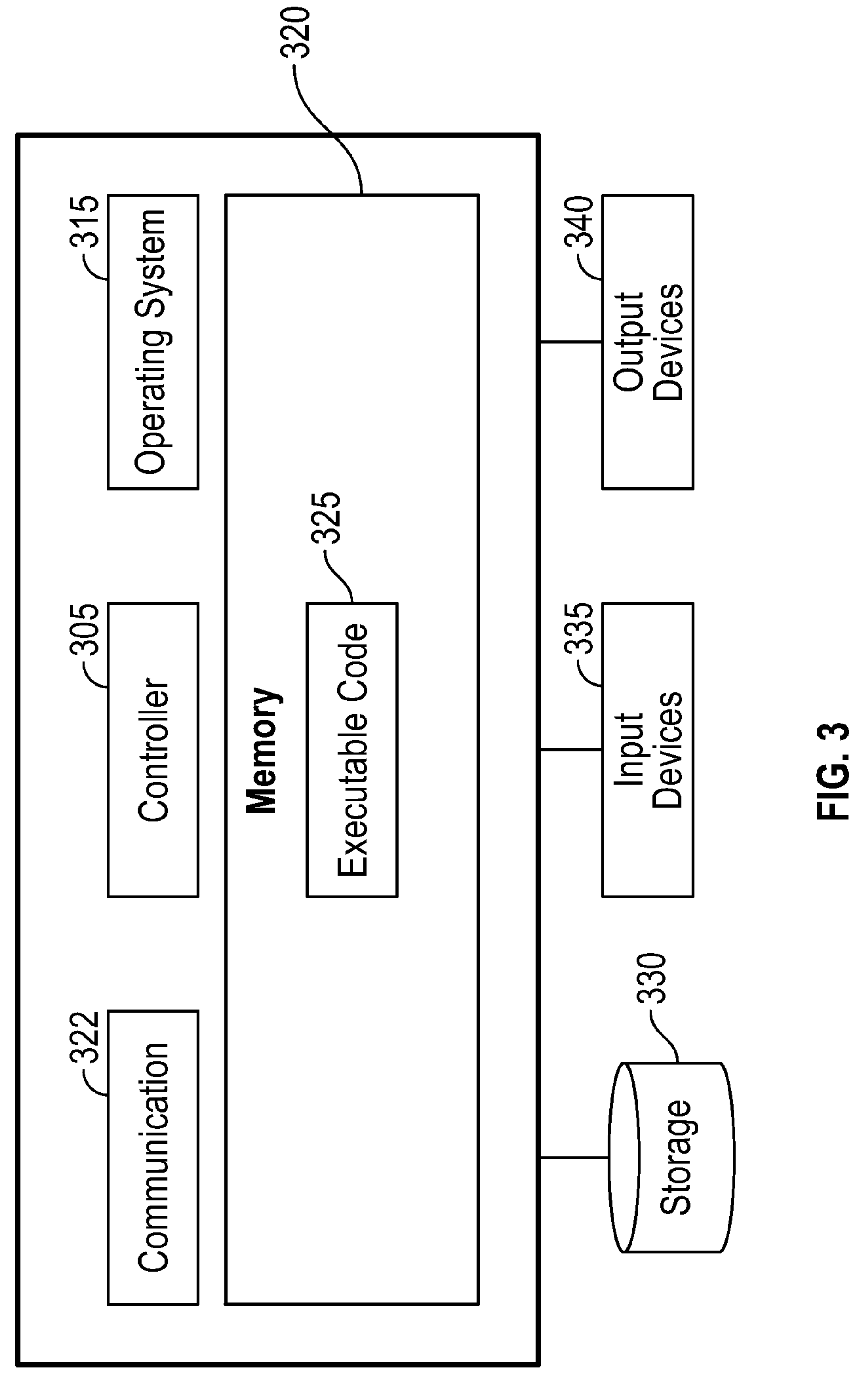
FIG. 3 is a block diagram of an exemplary computing system which may be used with the systems of the disclosure.

FIG. 3 shows a block diagram of an exemplary computing system 300 that may be used with image analyzing systems of the present disclosure. Computing system 300 may include a processor or controller 305 that may be or include, for example, one or more central processing unit processor (s) (CPU), one or more Graphics Processing Unit(s) (GPU or GPPP), a chip or any suitable computing or computational device, an operating system 215, a memory 320, a storage 330, input devices 335 and output devices 340. Modules or equipment for collecting or receiving (e.g., a receiver worn on a patient) or displaying or selecting for display (e.g., a workstation) medical images collected by the CE imaging device 212 (FIG. 2) may be or include, or may be executed by, the computing system 300 shown in FIG. 3. A communication component 322 of the computing system 300 may allow communications with remote or external devices, e.g., via the Internet or another network, via radio, or via a suitable network protocol such as File Transfer Protocol (FTP), etc.

The computing system 300 includes an operating system 315 that may be or may include any code segment designed and/or configured to perform tasks involving coordination, scheduling, arbitration, supervising, controlling or otherwise managing operation of computing system 300, for example, scheduling execution of programs. Memory 320 may be or may include, for example, a Random Access Memory (RAM), a read-only memory (ROM), a Dynamic RAM (DRAM), a Synchronous DRAM (SD-RAM), a double data rate (DDR) memory chip, a Flash memory, a volatile memory, a non-volatile memory, a cache memory, a buffer, a short term memory unit, a long term memory unit, or other suitable memory units or storage units. Memory 320 may be or may include a plurality of, possibly different memory units. Memory 320 may store for example, instructions to carry out a method (e.g., executable code 325), and/or data such as user responses, interruptions, etc.

Executable code 325 may be any executable code, e.g., an application, a program, a process, task or script. Executable code 325 may be executed by controller 305 possibly under control of operating system 315. For example, execution of executable code 325 may cause the display or selection for display of medical images as described herein. In some systems, more than one computing system 300 or components of computing system 300 may be used for multiple functions described herein. For the various modules and functions described herein, one or more computing systems

300 or components of computing system 300 may be used. Devices that include components similar or different to those included in the computing system 300 may be used, and may be connected to a network and used as a system. One or more processor(s) 305 may be configured to carry out methods of the present disclosure by for example executing software or code. Storage 330 may be or may include, for example, a hard disk drive, a floppy disk drive, a Compact Disk (CD) drive, a CD-Recordable (CD-R) drive, a universal serial bus (USB) device or other suitable removable and/or fixed storage unit. Data such as instructions, code, medical images, image streams, etc. may be stored in storage 330 and may be loaded from storage 330 into memory 320 where it may be processed by controller 305. In some embodiments, some of the components shown in FIG. 3 may be omitted.

Input devices 335 may include for example a mouse, a keyboard, a touch screen or pad or any suitable input device. It will be recognized that any suitable number of input devices may be operatively coupled to computing system 300. Output devices 340 may include one or more monitors, screens, displays, speakers and/or any other suitable output devices. It will be recognized that any suitable number of output devices may be operatively coupled to computing system 300 as shown by block 340. Any applicable input/output (I/O) devices may be operatively coupled to computing system 300, for example, a wired or wireless network interface card (NIC), a modem, printer or facsimile machine, a universal serial bus (USB) device or external hard drive may be included in input devices 335 and/or output devices 340.

Multiple computer systems 300 including some or all of the components shown in FIG. 3 may be used with the described systems and methods. For example, a CE imaging device 212, a receiver, a cloud-based system, and/or a workstation or portable computing device for displaying images may include some or all of the components of the computer system of FIG. 3. A cloud platform (e.g., a remote server) including components such as computing system 300 of FIG. 3 may receive procedure data such as images and metadata, processes and generate a study, and may also display the generated study for the doctor's review (e.g., on a web browser executed on a workstation or portable computer). An "on-premise" option, may use a workstation or local server of a medical facility to store, process and display images and/or a study.

According to some aspects of the present disclosure, a user (e.g., a physician), may build his or her understanding of a case by reviewing a study, e.g., a display of images (e.g., captured by the CE imaging device 212) that were selected, e.g., automatically, as images that may be of interest. In some systems of the present disclosure, a relatively small number of images from the captured images are displayed for the user's review per case. By "relatively small number" it is meant on the order of hundreds at most or at least at average as opposed to current methods, which display a video stream of images that typically includes thousands of images per a case (e.g., around 6,000 images). In some systems, only up to a few hundreds of images are displayed for the user's review. In some systems, the number of images displayed for the user's review is up to an order of 1,000. Browsing through a relatively small number of images, as opposed to watching or reviewing thousands of images, may significantly ease the review process for the user, reduce the reading time per case and may lead to better diagnosis. Aspects of exemplary user interfaces for displaying a study are described in co-pending International Patent Application Publication No. WO/2020/079696, entitled "Systems and Methods for Generating and Displaying a Study of a Stream of In-Vivo Images," which is hereby incorporated by reference in its entirety. Other aspects of the computing system 300 and the capsule system (210, FIG. 2) are described in co-pending U.S. Provisional Application No. 62/867,050, entitled "Systems and Methods For Capsule Endoscopy Procedure," which is hereby incorporated by reference in its entirety.

With reference to FIG. 4 an illustration of the colon 400 is shown. The colon 400 absorbs water and any remaining waste material is stored as feces before being removed by defecation. The colon 400 may be divided, for example, into five anatomical segments: cecum 404, right or ascending colon 410, transverse colon 416, left or descending colon 422 (e.g., left colon-sigmoid 424), and rectum 428.

An ileum 408 is the final section of the small bowel and leads to the cecum 404 and is separated from the cecum 404 by a muscle valve called the ileocecal valve (ICV) 406. The cecum 404 is the first section of the colon 400. The cecum 404 includes the appendix 402. The next portion of the colon 400 is the ascending colon 410. The ascending colon 410 is connected to the small bowel by the cecum 404. The ascending colon 410 runs upwards through the abdominal cavity toward the transverse colon 416.

The transverse colon 416 is the part of the colon 400 from the hepatic flexure, also known as the right colic flexure 414, (the turn of the colon 400 by the liver) to the splenic flexure also known as the left colic flexure 418, (the turn of the colon 400 by the spleen). The transverse colon 416 hangs off the stomach, attached to it by a large fold of peritoneum called the greater omentum. On the posterior side, the transverse colon 416 is connected to the posterior abdominal wall by a mesentery known as the transverse mesocolon.

The descending colon 422 is the part of the colon 400 from the left colic flexure 418 to the beginning of the sigmoid colon 426. One function of the descending colon 422 in the digestive system is to store feces that will be emptied into the rectum. The descending colon 422 is also called the distal gut, as it is further along the gastrointestinal tract than the proximal gut. Gut flora is generally very dense in this region. The sigmoid colon 426 is the part of the colon 400 after the descending colon 422 and before the rectum 428. The name sigmoid means S-shaped. The walls of the sigmoid colon 426 are muscular, and contract to increase the pressure inside the colon 400, causing the stool to move into the rectum 428. The sigmoid colon 426 is supplied with blood from several branches (usually between 2 and 6) of the sigmoid arteries.

The rectum 428 is the last section of the colon 400. The rectum 428 holds the formed feces awaiting elimination via defecation.

The CE imaging device 212 (FIG. 2) may be used to image the interior of the colon 400. The entrance from the small bowel into the colon 400 happens through the ICV 406. Usually after entering the colon 400 through the ICV 406, the CE imaging device 212 goes into the cecum 404. However, occasionally, the CE imaging device 212 misses the cecum 404 and goes straight into the ascending colon 410. The colon 400 may be wide enough to enable almost unrestricted CE imaging device 212 movement. The CE imaging device 212 may rotate and roll. The CE imaging device 212 may rest in one place for a long period of time, or it may move very fast through the colon 400.

In general, the division of the GIT into anatomical segments may be performed, for example, based on identifying that the CE imaging device 212 has passed between the different anatomical segments. Such identification may be performed, for example, based on machine learning techniques. Dividing of GIT images by GIT portions where the images were captured is addressed in co-pending U.S. Provisional Application No. 63/018,890, and dividing of colon image by colon portions where the images were captured is addressed in co-pending U.S. Provisional Application No. 63/018,878. The entire contents of both co-pending patent applications are hereby incorporated by reference. Other techniques for dividing of GIT images by GIT portions or colon portions where the images were captured will be understood by persons skilled in the art.

The following description relates to images of a colon captured by a capsule endoscopy device. Such colon images may part of a stream of images of the GIT and may be picked out from the stream of GIT images using the technology of the co-pending applications or using other methodologies which persons skilled in the art would understand.

Figure 5:
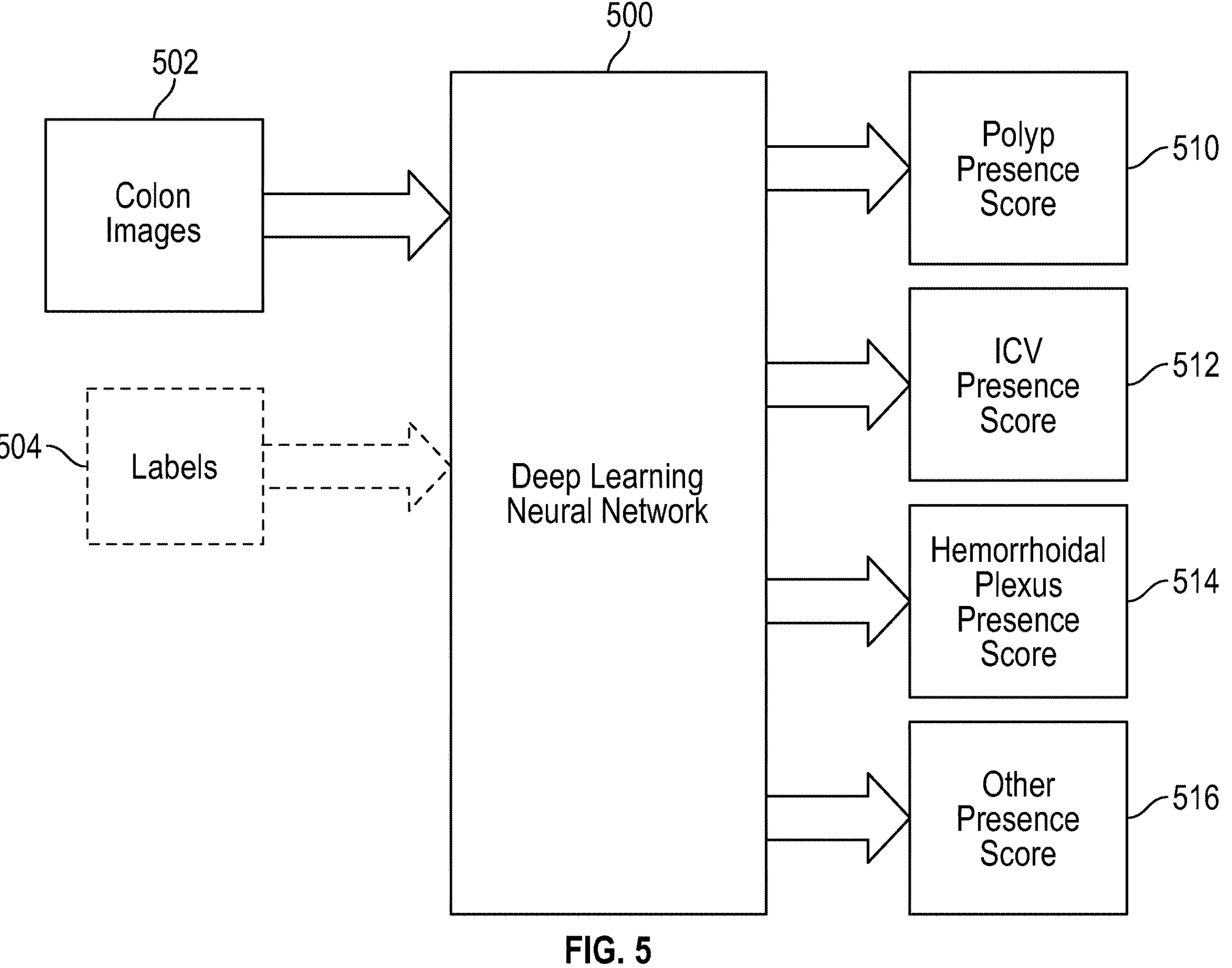
FIG. 5 is a diagram of an exemplary deep learning neural network, in accordance with aspects of the disclosure.

With reference to FIG. 5, there is shown a block diagram of a deep learning neural network 500 for providing classification scores of images. The images 502 are colon images. In the present disclosure, the term "classification score" or "score" may be used to describe a value or a vector of values generated by a machine learning system/model for a category or a set of categories applicable to an image/frame. The term "classification probabilities" or "probabilities" may be used to describe a transformation of classification scores into values which reflect probabilities that each category of the set of categories applies to the image/frame.

In some systems, the deep learning neural network 500 may include a convolutional neural network (CNN) and/or a recurrent neural network having "Long Short Term Memory" (LSTM), which will be described in more detail later herein. In machine learning, a CNN is a class of artificial neural network that is most commonly used to analyze images. The convolutional aspect of a CNN relates to applying matrix processing operations (called "kernels" or "filters") to localized portions of an image. The kernels/filters are computationally adjusted during supervised training of the CNN to identify characteristics of the input images that can be used to classify the images. A CNN typically includes convolution layers, activation function layers, and pooling (typically max pooling) layers to reduce dimensionality without losing too much information.

The deep learning neural network 500 may use one or more CNNs to provide classification scores for one or more colon images, taken by the CE imaging device 212 (see FIG. 2), for presence of one or more landmarks, colon characteristics, colon pathologies, or colon content (e.g., bubbles, etc.). For example, the deep learning neural network 500 can generate classification scores for an image for presence of a colon polyp 510, presence an ileocecal valve 512, presence of a hemorrhoidal plexus 514, or presence of other landmarks, characteristics, pathologies, or content 516 (e.g., colon bleeding). The deep learning neural network 500 may be executed on the computing system 300 (FIG. 3). Persons skilled in the art will understand the deep learning neural network 500 and how to implement it. Various deep learning neural networks can be used, including, without limitation, MobileNet or Inception.

The deep learning neural network 500 may be trained based on labeled training images. For example, an image may have a label 504 indicating the presence of a landmark, pathology, characteristic, or content, such as presence of a colon polyp, an ileocecal valve, or a hemorrhoidal plexus, among others things. The labels 504 are shown with dashed lines to indicate that it is used only for training the deep learning neural network 500 and are not used when operating the deep learning neural network 500 outside of training, i.e., for inference. The training may include augmenting the training images to include adding noise, changing colors, hiding portions of the training images, scaling of the training images, rotating the training images, a mirror flip of the training images, and/or stretching the training images. Persons skilled in the art will understand training the deep learning neural network 500 and how to implement the training.

The illustrative embodiment of FIG. 5 for providing classification scores is exemplary, and other ways of providing classification scores are contemplated to be within the scope of the present disclosure. For example, two or more deep learning neural networks (not shown) can operate to provide the classification scores 510-516 for the colon images 502. For example, one deep learning neural network may be configured to provide classification scores for presence of polyps 510, another deep learning neural network may be configured to provide classification scores for presence of ileocecal valve 512, and a third deep learning neural network may be configured to provide classification scores for presence of hemorrhoidal plexus 514. The classifications scores 510-516 can be provided by two or more deep learning neural networks in different configurations.

As another example, in various embodiments, unsupervised learning or another type of learning may be used. In various embodiments, the classification scores can be provided by various configurations of neural networks, by machine learning systems that are not neural networks (e.g., classical machine learning systems involving feature selection), and/or by classification techniques which persons skilled in the art will recognize. In various embodiments, machine learning systems or classification systems can provide classification probabilities rather than or in addition to classification scores. In various embodiments, classification scores can be converted to classification probabilities using techniques such as Platt scaling, SoftMax, or other techniques that will be recognized by persons skilled in the art. Such variations are contemplated to be within the scope of the present disclosure.

Figure 6:
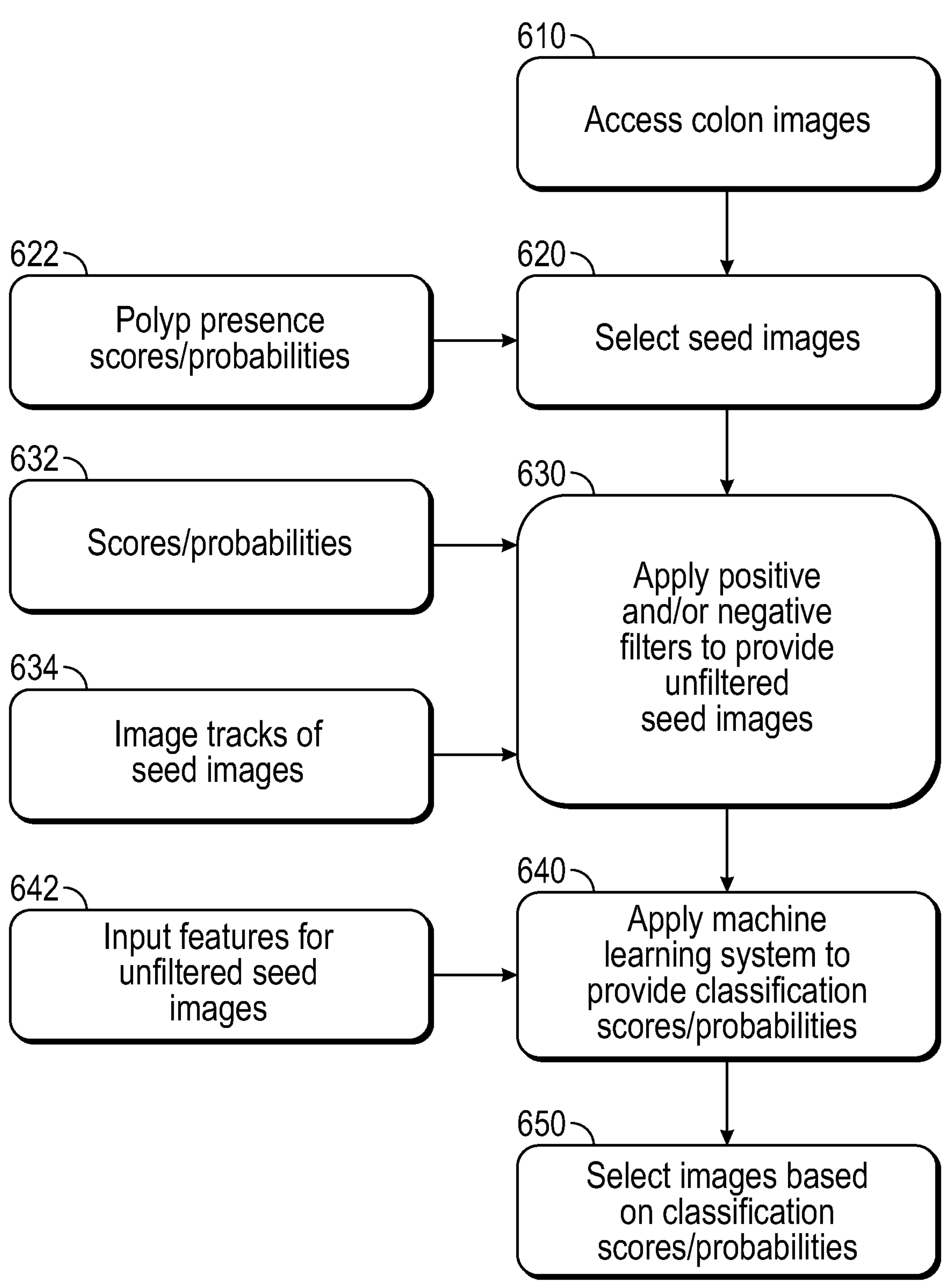
FIG. 6 is a block diagram of an exemplary operation for selecting colon images which contain a colon polyp with a high degree of confidence, in accordance with aspects of the present disclosure.

With reference to FIG. 6, there is shown a flow diagram of an exemplary operation for identifying images which contain a polyp. The operations of FIG. 6 can be performed by a computing system, such as the computing system of FIG. 2 and FIG. 3. Some or all blocks of FIG. 6 may be referred to as a polyp detection system. At block 610, the operation accesses various colon images captured by a capsule endoscopy device, such as the CE imaging device 212 of FIG. 2. At block 620, an initial image selection process is applied to the colon images to select various images as seed images. The selection process accesses polyp presence scores or probabilities 622, such as scores/probabilities provided by the deep learning neural network of FIG. 5.

Figure 7:
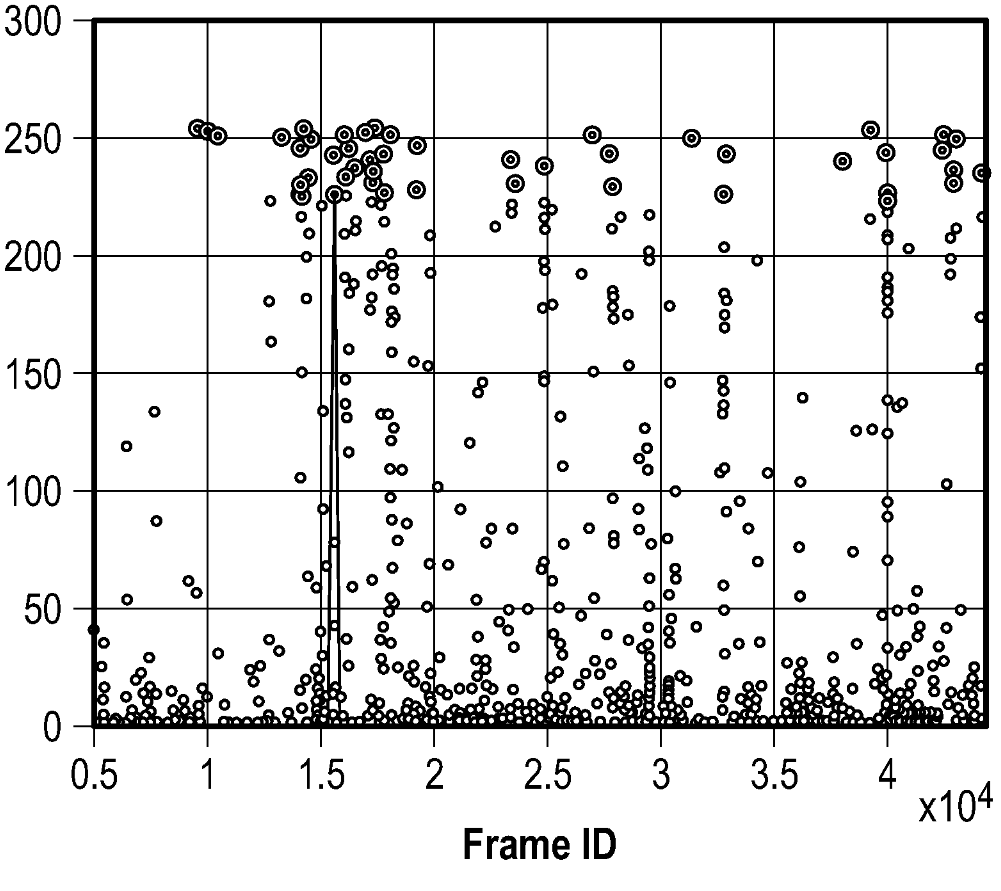
FIG. 7 is a diagram of selected seed images, in accordance with aspects of the disclosure.

Generally, the seed image selection process 620 selects images having the highest polyp presence scores, and the selection can be performed in various ways. Exemplary selection processes are described in International Application Publication No. WO2017199258 and U.S. Provisional Application No. 63/018,870, which are hereby incorporated by reference in their entirety, and which can be applied in the initial selection process of block 620. For example, and as a brief description, the initial selection process can be an iterative process. At each iteration, the process selects the image having the highest score/probability for presence of a polyp, and the selected image is referred to herein as a "seed image." The scores/probabilities of images that are around the seed image are decreased to reduce the chance of images of the same polyp being selected in subsequent iterations. The process iterates until a stopping criterion or stopping criteria are satisfied. For example, the iterative image selection process can terminate when no remaining image scores satisfy a score/probability threshold. As another example, the iterative image selection process can terminate when a particular number of seed images have been selected, such as sixty seed images or one-hundred seed images, for example. FIG. 7 illustrates a result of the iterative selection process in a graph in which the x-axis represents the index/ID number of an image and the y-axis represent the polyp presence score of an image. The images selected by the iterative process are shown by circles at the top of the graph. The result of the initial image selection process 620 is a set of seed images which have high polyp presence scores or probabilities. As mentioned above, the described image selection process is exemplary and other image selection methods and techniques are contemplated to be within the scope of the present disclosure.

The result of block 620 are seed images which have high polyp presence scores or probabilities. The operations of blocks 630-650 are described below, and such blocks may operate based on a tradeoff between sensitivity and specificity, which persons skilled in the art will understand. In the operation of block 620, the emphasis may be on sensitivity, even if it requires lowering specificity. In the operations of block 630-650, the emphasis may be on specificity, even if it requires lowering sensitivity.

With continuing reference to FIG. 6, at block 630, the seed images resulting from the initial image selection process are processed by negative filters and/or positive filters. As used herein, a positive filter is an operation which positively designates seed images that satisfy one or more criteria as a seed image that contains a polyp. A negative filter, on the other hand, is an operation which identifies seed images that satisfy one or more criteria as a seed image which should not be positively designated as containing a polyp. In various embodiments, a negative filter does not designate a seed image as not containing a polyp. In various embodiments, a negative filter may designate a seed image as not containing a polyp. Block 630 may apply one or more positive filters and/or one or more negative filters, which will be described in more detail later herein. For now, it is sufficient to note that various filters may use scores or probabilities 632, such as classification scores or probabilities provided by the deep learning neural network of FIG. 5. Additionally, various filters may use image tracks 634, which will be described in connection with FIG. 10 and FIG. 11. The filters may be implemented using heuristics or using a machine learning system, such as a deep learning neural network or a classical machine learning system, among others. The result of block 630 may include seed images which have been designated by a positive filter as being seed images containing polyps, seed images which have been identified by a negative filter, and seed images which have neither been designated by a positive filter nor identified by a negative filter. The last group of seed images—which have neither been designated by a positive filter nor identified by a negative filter—will be referred to herein as "unfiltered" seed images. The unfiltered seed images are processed by block 640.

At block 640, the unfiltered seed images resulting from block 630 are processed by a machine learning system which operates to provide a classification score or probability indicative of whether an unfiltered seed image contains a polyp or does not contain a polyp. The machine learning system accesses input features 642 associated with the unfiltered seed images, which will be described in more detail later herein. In various embodiments, the machine learning system may be a classical machine learning system and can be trained by supervised learning, unsupervised learning, or another type of learning. In various embodiments, the machine learning system may be a soft margin polynomial support vector machine with degree n, which can be degree 2, degree 3, or another degree. As mentioned above, the output of the machine learning system is a classification score or probability indicative of whether an unfiltered seed image contains a polyp or does not contain a polyp. Persons skilled in the art will understand how to implement such machine learning systems and train such machine learning systems based on input features.

At block 650, the process identifies images which have a high degree of confidence of containing a polyp based on the classification scores or probabilities provided by the machine learning system. Various thresholds can be applied to the classification scores or probabilities. For example, in various embodiments, images which have a classification probability of greater than 99% of containing a polyp can be selected in block 650. The result of block 650 are images which were not designated by a positive filter as an image containing a polyp but which had a high degree of confidence of containing a polyp based on machine learning classification scores or probabilities. Such images selected by block 650 can be used in various ways which will be described later herein. In various embodiments, images which were designated by a positive filter in block 630 as containing a polyp can also be used in various ways, as described later herein.

Figure 8:
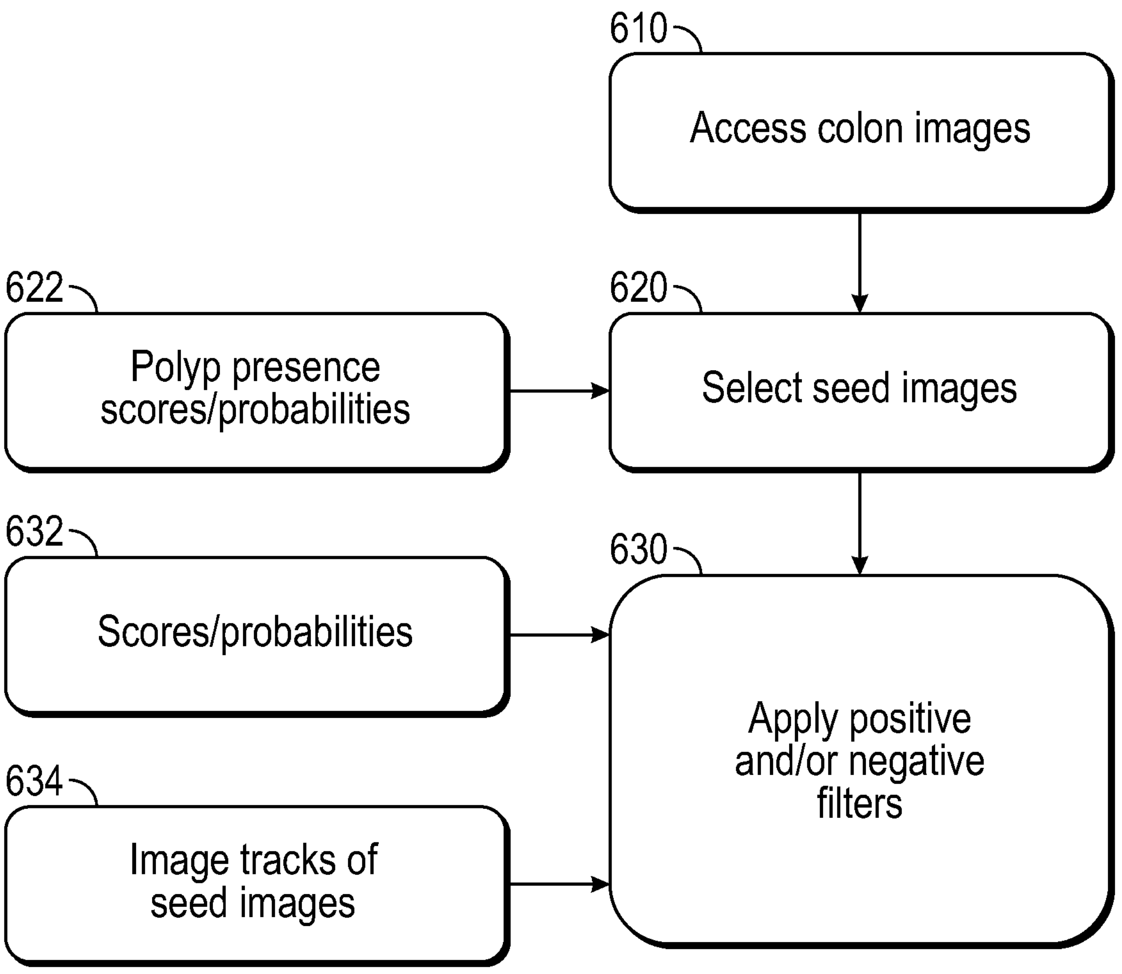
FIG. 8 is a block diagram of an exemplary operation to select colon images which contain a polyp, in accordance with aspects of the disclosure.
Figure 9:
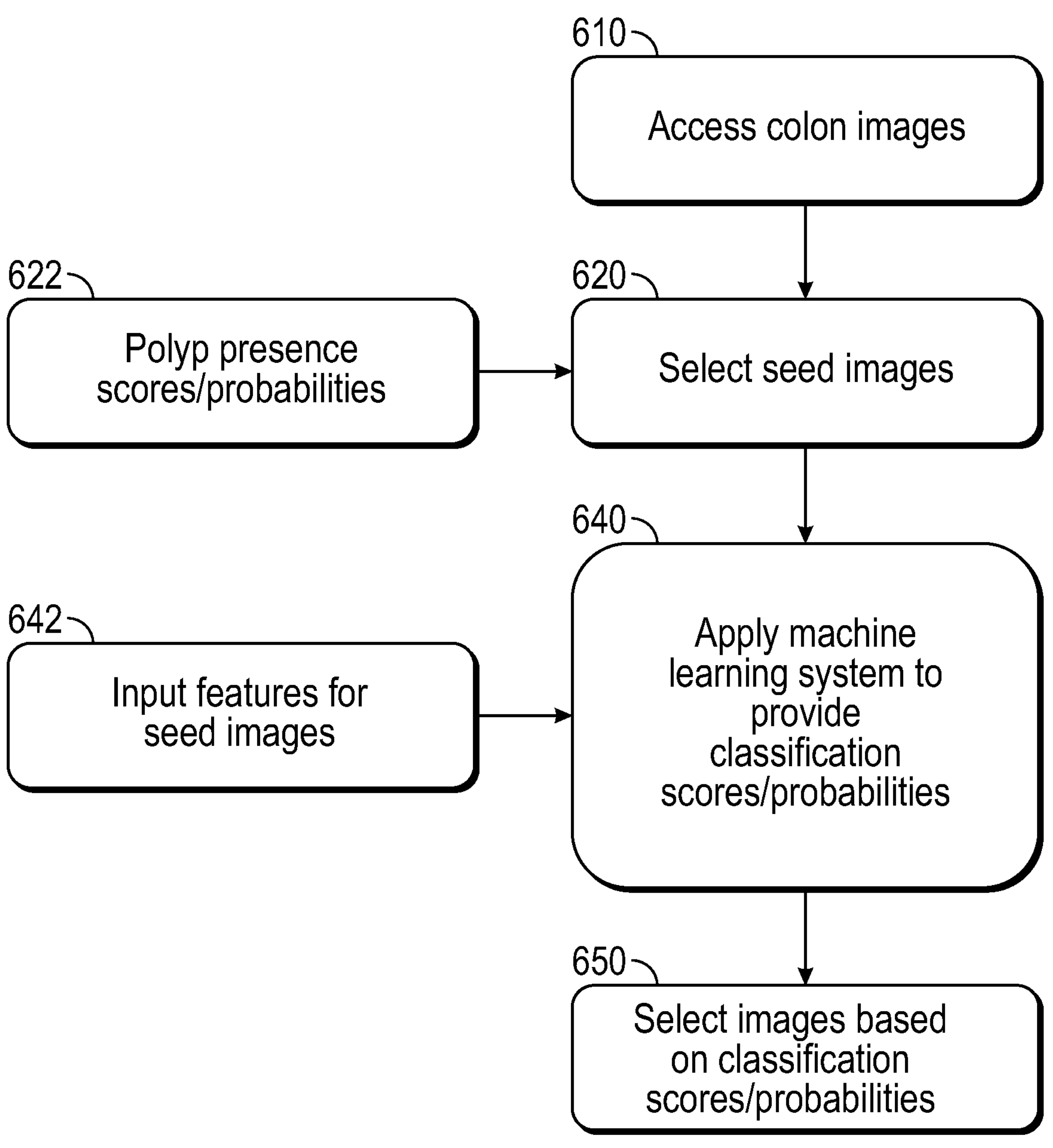
FIG. 9 is a block diagram of another exemplary operation for selecting colon images which contain a polyp, in accordance with aspects of the disclosure.

The embodiment of FIG. 6 is exemplary and variations are contemplated to be within the scope of the present disclosure. For example, in various embodiments, the process need not perform blocks 640 and 650 and can, instead, end at block 630, as shown in FIG. 8. In the embodiment of FIG. 8, the result of block 630 can be seed images which were designated by a positive filter as containing a polyp and/or the unfiltered seed images. As another variation of FIG. 6, in various embodiments, block 630 may not be performed, as shown in FIG. 9. In the embodiment of FIG. 9, the machine learning system would be applied to all seed images 640 and would access input features associated with the seed images 642. Such variations and other variations are contemplated to be within the scope of the present disclosure.

The following will describe various positive filters and negative filters which could be applied in the block 630 of FIG. 6 and FIG. 8.

As shown in FIGS. 6 and 8, various filters access and use image tracks of seed images 632. As used herein, a "track" refers to a collection of consecutive images across which a polyp in a seed image has been tracked by a consecutive-image tracker. As mentioned above, the phrase "consecutive images" means images which, when ordered in a sequence, are adjacent to each other in the sequence. A "consecutive image tracker" refers to object tracking techniques which are designed to identify small changes in an object between consecutive images/frames and which can identify whether seed images close to each other may contain the same polyp. Such tracking technologies include optical flow techniques, for example. Persons skilled in the art will understand how to implement optical flow techniques. Other technologies for tracking objects in consecutive images are contemplated to be within the scope of the present disclosure.

Figure 10:
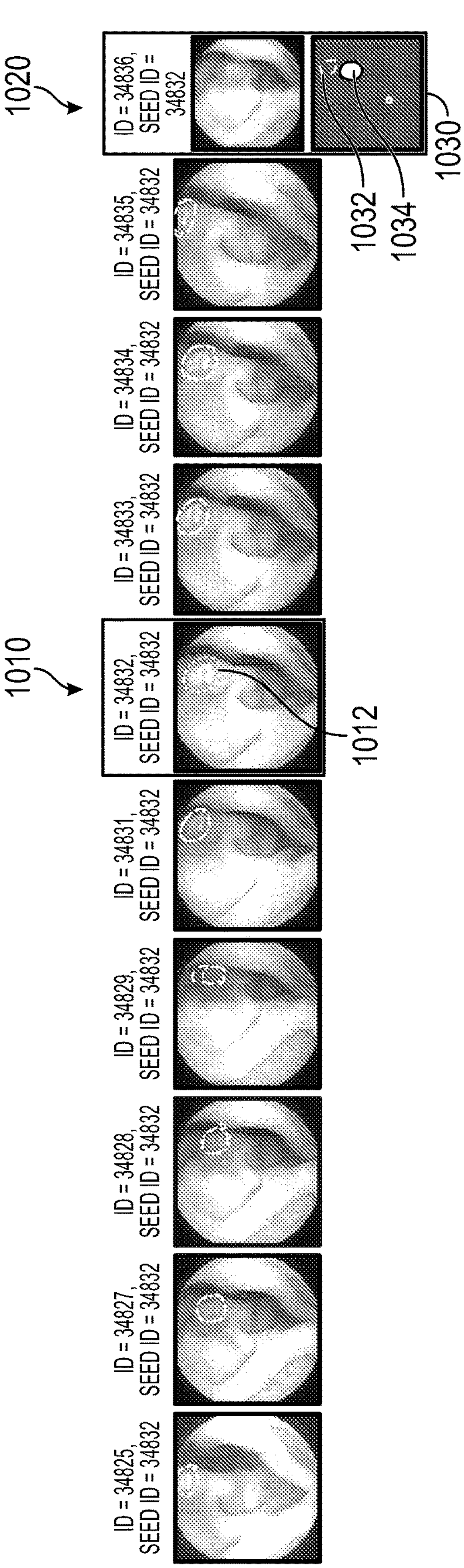
FIG. 10 is a diagram of an exemplary image track for a seed image, in accordance with aspects of the disclosure.

FIG. 10 shows an example of applying a consecutive-image tracker to a seed image to identify a track for the seed image. Starting with the seed image 1010, the consecutive-image tracker processes adjacent images to track the polyp 1012. In the illustrated example, the polyp 1012 is tracked across five frames before the seed image 1010 and across three frames after the seed image 1010. At the fourth frame 1020 after the seed image 1010, the tracking ends by operation of the tracking technology. A graphical representation 1030 of the tracking technology shows that the expected location 1032 of the polyp is off from the actual location 1034 of the polyp. Therefore, the polyp 1012 was not tracked to that frame 1020. The track for the seed image 1010 is the collection of consecutive frames in FIG. 10 (without frame 1020), across which the polyp 1012 in the seed image 1010 was tracked by a consecutive-image tracker. The track includes the seed image 1010. Thus, in FIG. 6 and FIG. 8, a track is accessed for each seed image 632, and the track can be used by various positive and/or negative filters. The embodiment of FIG. 10 is exemplary. In various embodiments, a "track" may be identified using other technologies for comparing two images, such as technology for comparing two images using a classification system, which is described in co-pending U.S. Provisional Application No. 63/073,544, filed Sep. 2, 2020. Such provisional application is hereby incorporated by reference in its entirety.

As described above, a positive filter is an operation which positively designates seed images that satisfy one or more criteria as a seed image that contains a polyp. In accordance with aspects of the present disclosure, a positive filter may have a criterion that a seed image having a polyp presence score or probability 622 that is greater than or equal to a threshold value will be designated as a seed image containing a polyp. In various embodiments, the polyp presence score may be normalized to a value between 0 and 1. A polyp presence probability is naturally between 0 and 1. In various embodiments, the threshold value may be 0.999999 or 0.9999999 or another value which provides a high degree of certainty that the seed image contains a polyp.

Figure 11:
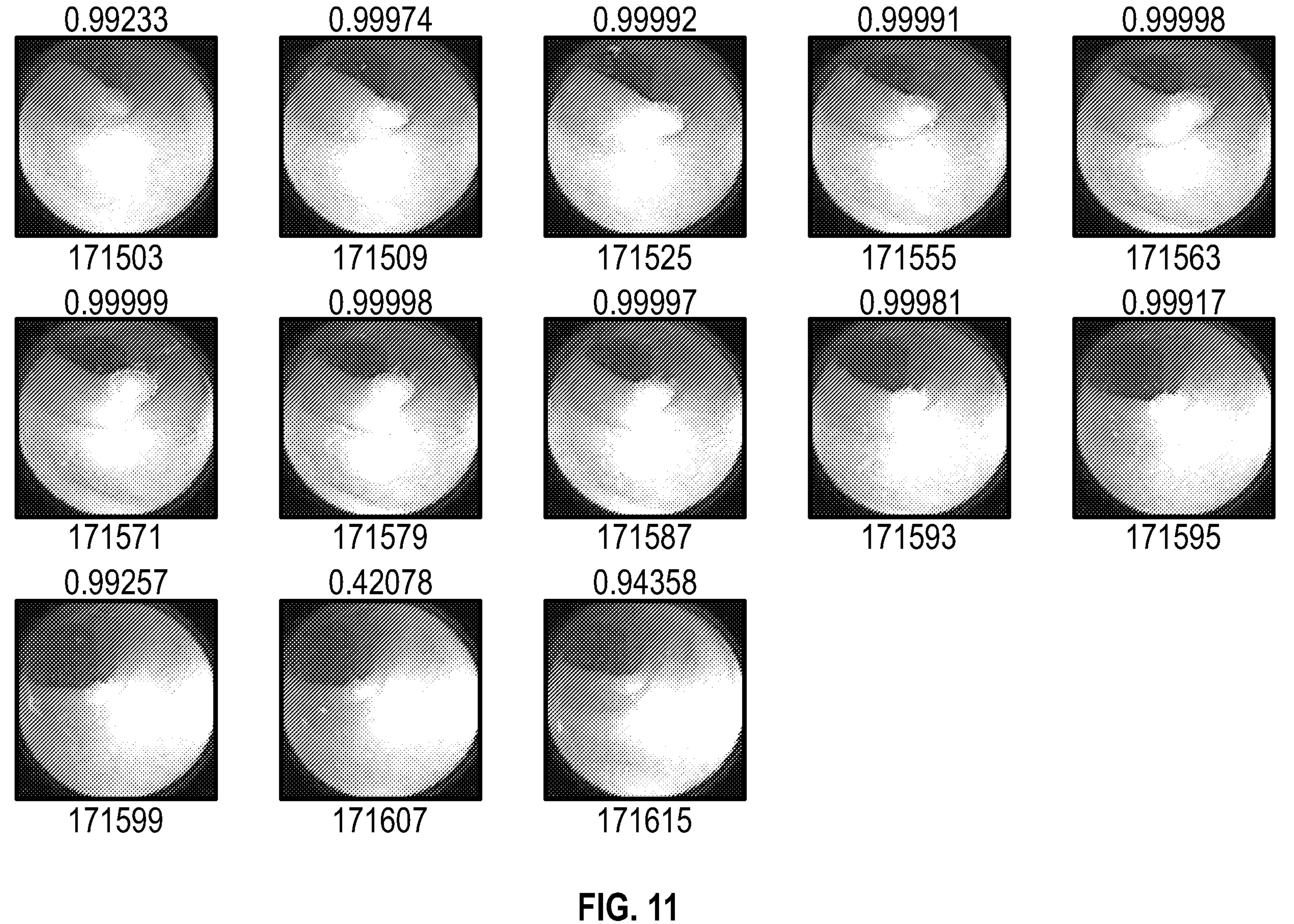
FIG. 11 is a diagram of an exemplary image track processed by a positive filter, in accordance with aspects of the disclosure.

In various embodiments, a positive filter may have a further criterion that the track of a seed image includes at least a particular number of consecutive images whose polyp presence scores or probabilities are greater than or equal to a threshold value. In various embodiments, the threshold value for the seed image and for images in the track may be the same value. In various embodiments, the threshold value for the seed image and for images in the track may be different values. As an example, a positive filter may designate a seed image as containing a polyp when the seed image has a polyp presence score/probability of at least 0.99999 and at least five consecutive frames adjacent to the seed image also have polyp presence scores/probabilities of at least 0.9999. FIG. 11 shows an example of such a seed image and track, where the seed image is identified by frame number 171571. The seed image has a polyp presence score of 0.99999 and five consecutive frames adjacent to the seed image have polyp presence scores of at least 0.9999. Thus, the seed image of FIG. 11 is designated by a positive filter as containing a polyp.

The positive filters described above are exemplary. Other positive filters for positively designating an image as containing a polyp are contemplated to be within the scope of the present disclosure. For example, track information may be used in other ways to form a positive filter. As described above, a track includes a collection of images, and such images are captured over time by a capsule endoscopy device (e.g., 212, FIG. 2). Information of a temporal nature can be processed using Long Short Term Memory (LSTM). A deep learning neural network, such as the deep learning neural network 500 of FIG. 5, can be configured to receive a track of images as an input. The deep learning neural network can be trained to provide a classification score or probability for a seed image based on the image track that is received by the deep learning neural network. The classification score or probability can be, for example, a score of probability of the seed image containing a polyp.

As described above, a negative filter is an operation which identifies seed images that satisfy one or more criteria as a seed image which should not be positively designated as containing a polyp. In various embodiments, a negative filter does not designate a seed image as not containing a polyp. In various embodiments, a negative filter may designate a seed image as not containing a polyp.

As shown in FIG. 6 and FIG. 8, a negative filter may access classification scores or probabilities 632, such as classification scores or probabilities provided by the machine learning system of FIG. 5. In accordance with aspects of the present disclosure, a negative filter can access an ileocecal valve (ICV) presence score or probability (e.g., 512, FIG. 5) and can operate to identify seed images which have an ICV score or probability above a threshold value, such as an ICV probability above 0.99999, for example, or above another threshold value. An ileocecal valve is an anatomical landmark at the transition from the small bowel to the colon and may be similar in appearance to a large colon polyp, such that a seed image may have a sufficiently high polyp presence score or probability to be a seed image while also having an ICV presence score that is above a predetermined threshold. Such a seed image can be identified by a negative filter as satisfying criteria. The negative filter may designate the seed image as not containing a polyp.

In accordance with aspects of the present disclosure, a negative filter can access a hemorrhoidal plexus presence score or probability (e.g., 514, FIG. 5). The hemorrhoidal plexus is an anatomical landmark which surrounds the rectum, at the end of the colon, and may be similar in appearance to a colon polyp. In various embodiments, the negative filter can operate to identify seed images which have a hemorrhoidal score or probability above a threshold value, such as a hemorrhoidal probability above 0.99999, for example, or above another threshold value. A seed image may have a sufficiently high polyp presence score or probability to be a seed image while also having a hemorrhoidal plexus presence score that is above a predetermined threshold. Such a seed image can be identified by a negative filter as satisfying criteria. The negative filter may designate the seed image as not containing a polyp.

In various embodiments, rather than accessing a hemorrhoidal plexus presence score or probability, a negative filter can instead operate to determine the proximity of a seed image to a body exit/exit of the gastrointestinal tract. The proximity of a seed image to the body exit can be determined in various ways. For example, the negative filter can access colon images (e.g., colon images accessed in block 610 of FIG. 6) and can determine proximity of the seed image to the body exit by whether the seed image is within a final portion of the colon images, such as whether the seed image is within a final 0.5% of the colon images or within another final percentage of the colon images. If the seed image is within a final portion of the colon images, the negative filter can identify the seed image as satisfying criteria. In various embodiments, the negative filter may designate the seed image as not containing a polyp. In various embodiments, the negative filter may identify the seed image as satisfying criteria but may not designate the seed image as not containing a polyp.

In accordance with aspects of the present disclosure, a negative filter can access image tracks for seed images, such as image tracks described in connection with FIG. 10. A negative filter can have a criterion of identifying a seed image when the seed image is the only image in the track that has a polyp presence score or probability that is above a threshold value. For example, when the seed image of an image track has a polyp presence probability of at least 0.998 and every other image in the image track has a polyp presence probability less than 0.998, the seed image can be identified as satisfying criteria. Other threshold values can be used. In various embodiments, the negative filter may designate the seed image as not containing a polyp. In various embodiments, the negative filter may identify the seed image as satisfying criteria but may not designate the seed image as not containing a polyp.

In accordance with aspects of the present disclosure, a negative filter can access an estimated polyp size for a seed image. The negative filter can have a criterion of identifying a seed image when the estimated polyp size for a seed image is less than a threshold value, such as when the estimated polyp size is less than 3.5 mm or less than another threshold value. Various techniques can be used for generating the estimated polyp size that is accessed by the negative filter. An example of a technique is disclosed in U.S. patent application No. 63/075,782, which is hereby incorporated by reference in its entirety. Other techniques for estimating polyp size of a polyp in an image will be understood by persons skilled in the art. Such other techniques are contemplated to be within the scope of the present disclosure.

Accordingly, various positive filters and negative filters have been described above. Such filters can be applied in block 630 of FIG. 6 and FIG. 8. In the operation of FIG. 6, seed images which are neither designated by a positive filter nor identified by a negative filter (i.e., unfiltered seed images), can be processed by the machine learning system of block 640, as described above. In the operation of FIG. 8, block 630 is the end of the operation and can provide seed images which are designated by a positive filter and, in some embodiments, can also provide unfiltered seed images.

The following will describe exemplary input features for the machine learning system, which are accessed in block 642 of FIG. 6 and FIG. 9. As described above, the machine learning system operates based on the input features to provide a classification score or probability indicative of whether an unfiltered seed image contains a polyp or does not contain a polyp. In various embodiments, the machine learning system may be a soft margin polynomial support vector machine with degree n. In various embodiments, the machine learning system may be based on another classical machine learning model, such as decision tree, naïve Bayes, or logistic regression, among others, which persons skilled in the art will recognize. As described below, some input features can be based on the image track of a seed image, such as an image track as shown in FIGS. 10 and 11.

In accordance with aspects of the present disclosure, one of the input features to the machine learning system can be a seed polyp score/probability that is provided by a polyp detector, such as a detector as shown in FIG. 5.

In accordance with aspects of the present disclosure, one of the input features to the machine learning system can be a seed polyp score/probability that is determined based on a voting or an operation on polyp scores/probabilities provided by an ensemble of polyp detectors (e.g., FIG. 5) whose input is an image and whose output is the probability that the image contains a polyp. For example, the seed polyp score may be a mean of the polyp scores/probabilities provided by the ensemble of polyp detectors, or may be provided by another operation such as a median, among others.

In accordance with aspects of the present disclosure, one of the input features to the machine learning system can be the number of images in the image track for the seed image, which can be referred to as track length.

In accordance with aspects of the present disclosure, one of the input features to the machine learning system can be a number of images in the image track of the seed image that have a polyp presence score or probability that is greater than a threshold value, such as polyp presence probability greater than 0.998 or greater than another threshold value.

In accordance with aspects of the present disclosure, one of the input features to the machine learning system can be the difference in image index/ID number between the index/ID number of the seed image and the index/ID number of an image of the beginning of the colon. In various embodiment, an image of the beginning of the colon can be an image of the ICV. An image of the beginning of the colon can be determined in various way. For example, ICV presence scores or probabilities (e.g., 512, FIG. 5) can be used to determine images of the ICV. As another example, and as mentioned above, dividing of GIT images by GIT portions where the images were captured is addressed in co-pending U.S. Provisional Application No. 63/018,890, and dividing of colon images by colon portions where the images were captured is addressed in co-pending U.S. Provisional Application No. 63/018,878. Such technologies for dividing of GIT images into portions can be used to identify an image of the beginning of a colon. Other techniques for identifying images of the beginning of a colon are contemplated to be within the scope of the present disclosure.

In accordance with aspects of the present disclosure, one of the input features to the machine learning system can be localization information in terms of the colon segment in which the seed image was captured (represented as a number). As described in connection with FIG. 4, the colon 400 includes five anatomical segments: cecum, right or ascending colon, transverse colon, left or descending colon, and rectum. These five segments can be numbered one through five, respectively. The segment number of the colon segment in which the seed image was captured can be an input feature to the machine learning system. As mentioned above, dividing of colon images by colon portions where the images were captured is addressed in co-pending U.S. Provisional Application No. 63/018,878. Such technology for dividing of colon images by colon portions where the images were captured can be used to identify a number of the colon segment in which the seed image was captured. Other techniques for identifying the number of the colon segment in which the seed image was captured will be understood by persons skilled in the art and are contemplated to be within the scope of the present disclosure.

Accordingly, various input features for input to a machine learning system have been described. Persons skilled in the art will understand how to train and implement the machine learning system based on such input features. In various embodiments, not all of the described input features need to be used and various combinations of the input features may be used. In various embodiments, all of the described input features may be used. Some or all of the input features may be normalized in various ways. The described input features are exemplary and other input features are contemplated to be within the scope of the present disclosure.

Referring again to FIG. 6 and FIG. 8, the machine learning system of block 640 processes the input features and provides classification scores or probabilities indicating whether each of the seed images contains a polyp or does not contain a polyp. Classification probabilities can be used directly to determine which seed images have a sufficiently high probability to be selected as a seed image containing a polyp. Classification scores can be converted to classification probabilities in various ways, such as by Platt scaling, SoftMax, or other techniques, which persons skilled in the art will recognize. Seed images which are designated as containing a polyp can be used in various ways, as explained below in connection with FIG. 12.

In accordance with aspects of the present disclosure, the operations of FIG. 6, FIG. 8, and FIG. 9 can be enhanced in various ways. For example, additional rules (e.g., adjusted polyp detector score threshold) may be added which are based on the polyp size estimation, e.g., to comply with polyp size-related local medical guidelines/practice/policy. For example, U.S. medical practice is often based on at least one polyp of or above certain size whereas European medical practice is often based on multiple polyps of any size. Other countries may have different medical practices, and additional rules may be tailored to the medical practices of particular countries.

Accordingly, the description above provides systems and methods for identifying images containing polyps with a high degree of confidence. The following describes exemplary uses of the identified images.

Figure 12:
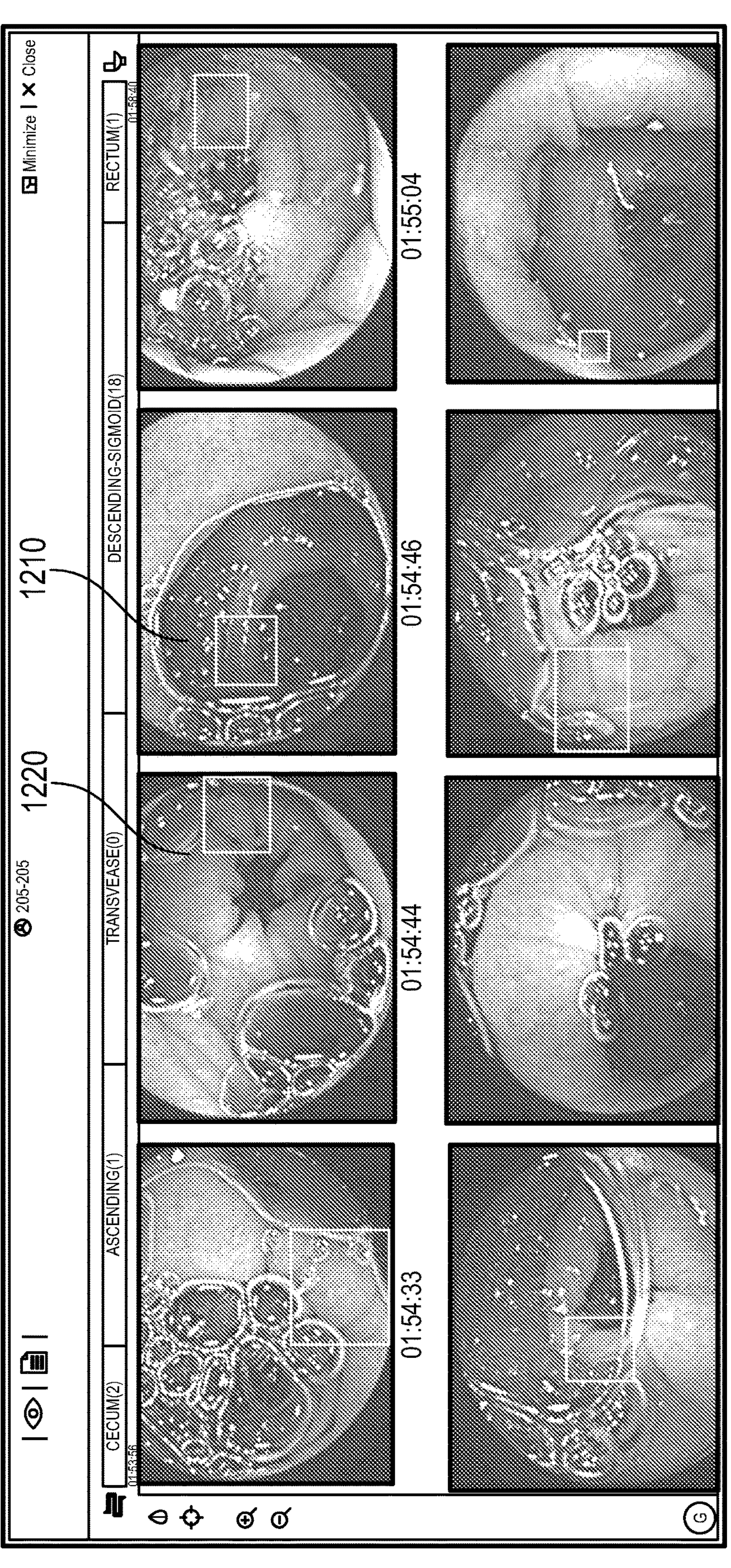
FIG. 12 is an exemplary display screen and user interface for a clinician to review and/or select colon images which may contain a colon polyp, in accordance with aspects of the disclosure.

Referring now to FIG. 12, there is shown an exemplary display screen for presenting images of polyps to a clinician. A GUI (or a study viewing application) may be used for displaying a study for a user's review and for generating a study report (or a CE procedure report). The screen of FIG. 12 displays a set of still images included in the study. The images may be, for example, seed images selected in block 620 of FIG. 6, FIG. 8, or FIG. 9. The user may review images and select one or more images which are of interest, e.g., displaying one or more polyps. The study images are displayed according to their location in the colon. The location may be any one of the following five anatomical colon segments: cecum, ascending, transverse, descending-sigmoid and rectum. The screen shows study images identified to be located in the descending-sigmoid. The user may switch between display of images located in the different segments. The illustrated display screen may be used by the user, e.g., a clinician, to select the images to be included in the study report. In some embodiments, the study may also include the tracks associated with the seed images (i.e., the study seed images). In such a case, a user may request (via user input) to display a track related to a displayed image (not shown). By reviewing the associated track, the clinician may receive further information relating to the seed image, which may assist the clinician in determining if the seed image (or optionally any other track image) is of interest.

With continuing reference to FIG. 12, a clinician may add bounding boxes around polyps observed in the images. A bounding box 1210 that is added by a user can appear in a particular color, such as a green color or another color. In accordance with aspects of the present disclosure, images containing polyps which are identified by the systems and method of the present disclosure can be presented to the clinician and bounding boxes 1220 can be automatically added to such images to display the location of the polyps. The bounding boxes 1220 added by the systems and methods of the present disclosure can appear in a different color than the bounding boxes added by a user, such as a red color or another color. In this way, the user can easily see which bounding boxes were added by users and which bounding boxes were automatically added.

Figure 13:
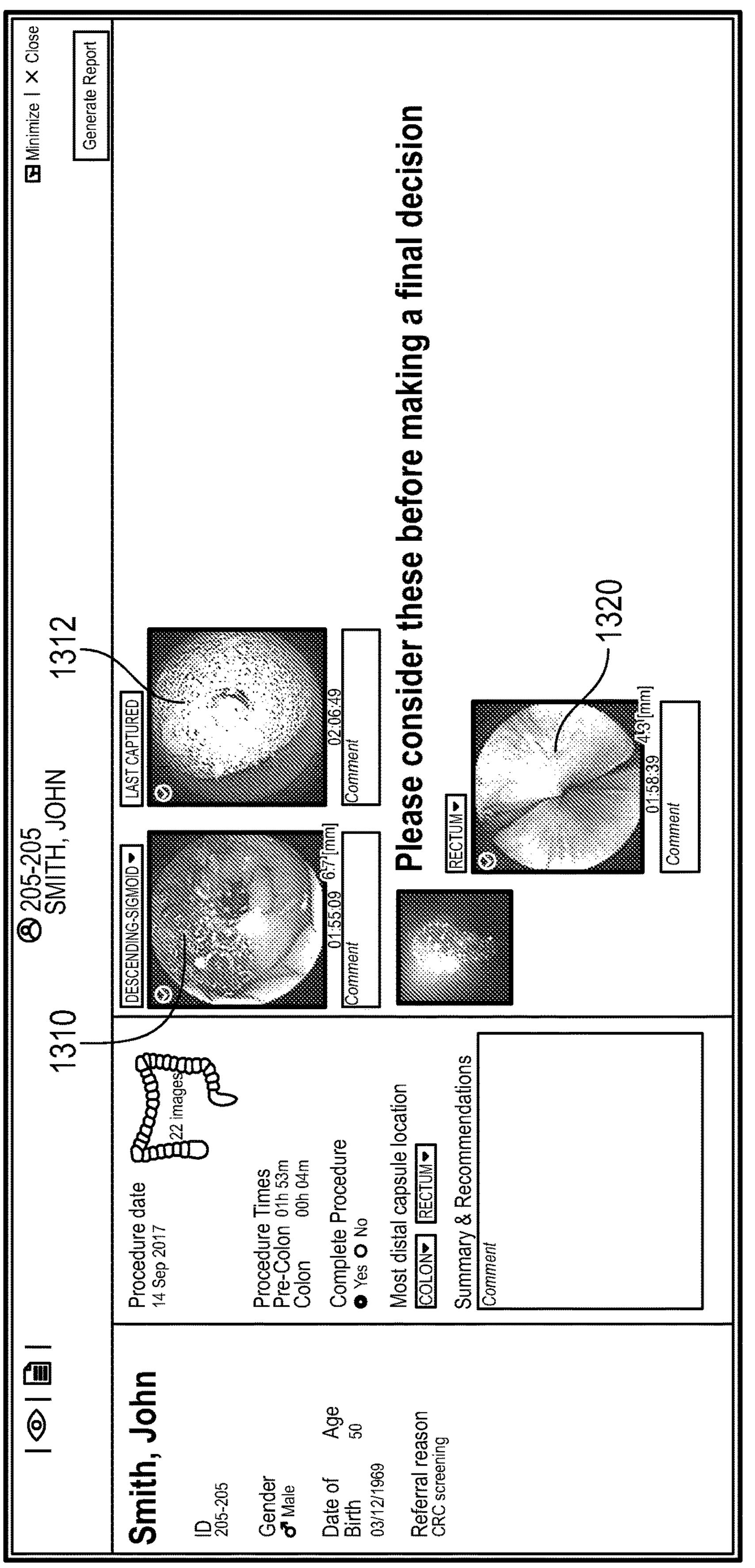
FIG. 13 is an exemplary display screen and user interface for presenting to a clinician a suggested image containing a polyp, in accordance with aspects of the disclosure.

Referring now to FIG. 13, there is shown an exemplary display screen for suggesting images of polyps to a clinician. The display screen shows images 1310, 1312 which have been selected by a clinician as containing a polyp and which the clinician would like to include in a final capsule endoscopy procedure report. Before the clinician finalizes the selections, the systems and methods of the present disclosure can display suggested images of polyps 1320 which the clinician may have missed or not selected. The suggested images 1320 may be images which were designated by a positive filter as an image containing a polyp (e.g., block 630, FIGS. 6 and 8) or images which were selected at block 650 (FIGS. 6 and 9) as having sufficiently high classification scores or probabilities for containing a polyp. In various embodiments, the suggested images 1320 may include unfiltered seed images as well. In various embodiments, the suggested images of polyps 1320 can be limited to GIT segments which do not contain any frames of polyps selected by a clinician or limited to GIT segments which the clinician has identified only smaller sized polyps (e.g., less than 6 mm). In various embodiments, if a GIT segment includes an image of a polyp selected by the clinician (e.g., 6 mm) and the systems of the present disclosure identify an image of a smaller polyp (e.g., 5 mm), the systems of the present disclosure may not suggest the smaller polyp to the clinician. Thus, in various embodiments, images which provide additional clinical value (e.g., according to medical practice guidelines) can be suggested while images which do not provide additional clinical value may not be suggested.

Figure 14:
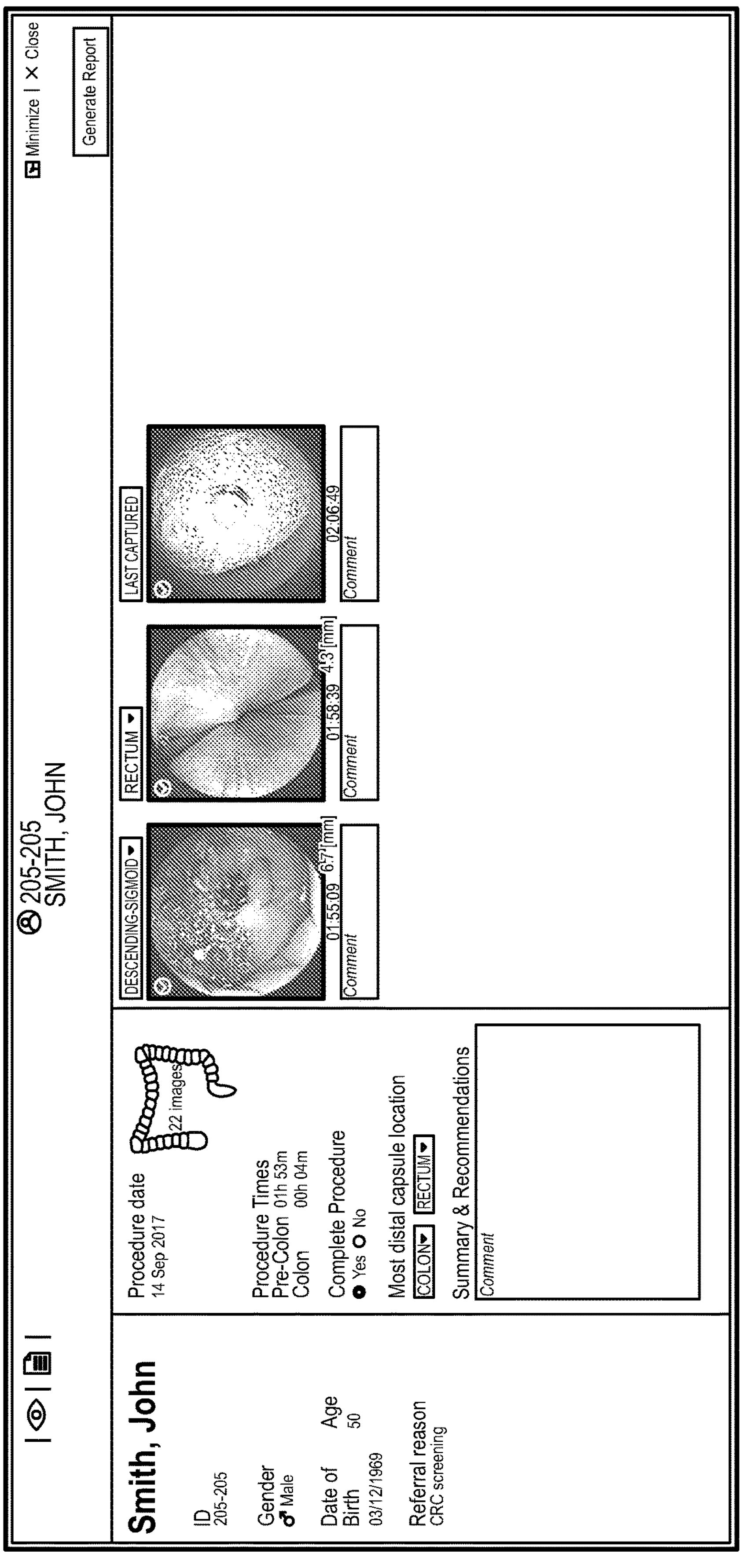
FIG. 14 is an exemplary display screen for a fully automatic process to present selected colon images containing polyps, in accordance with aspects of the present disclosure.

Referring to FIG. 14, there is shown an exemplary display screen that can be automatically generated by the systems and methods of the present disclosure without any human intervention or input. In contrast to the display screen of FIG. 13, which contained images 1310, 1312 selected by a user, the images of polyps in FIG. 14 can be automatically selected without human input. The automatically selected images may be images which were designated by a positive filter as an image containing a polyp (e.g., block 630, FIGS. 6 and 8) or images which were selected at block 650 (FIGS. 6 and 9) as having sufficiently high classification scores or probabilities for containing a polyp. In various embodiments, the display screen may always display a page of all suggested polyps regardless of any clinician selections or decisions, and such a display screen may be available to the user or clinician before or after the clinician reviews any images. In various embodiments, the automated selection of FIG. 14 may not select unfiltered seed images. In various embodiments, the systems and methods of the present disclosure may skip the display screen of FIG. 14 and may automatically generate and finalize a capsule endoscopy procedure report without any input or intervention by a clinician.

FIGS. 12-14 show possible uses of the images selected by the processes of FIGS. 6, 8, and 9. The embodiments of FIGS. 12-14 are exemplary and such display screens do not limit the scope of the present disclosure. Other uses are contemplated. In various embodiments, the systems and methods of the present disclosure can be used to overrule decisions by other tools to exclude a CE procedure, such as the tool described in U.S. Provisional Application No. 63/075,778, which is hereby incorporated by reference in its entirety. Such tool provides an adequacy measure which indicates a measurement for effectiveness of the CE procedure in capturing a predefined event in the plurality of images. In various embodiments, the adequacy measure for the procedure is determined based on a characteristic measure, which can include a plurality of measures that indicate a probability of at least one of capturing or not capturing the predefined event. The plurality of measures can include (i) a segment adequacy probability based on multiplying at least two of: a motion score, a cleansing level per segment, or a transit time, (ii) a global adequacy measure based on at least one of: an average cleansing score over all of the segments, a demographic of a patient, a last segment of the GIT that the CE device reached, or an absolute time the CE device spent in the portion of the GIT, and/or (iii) at least one of: an anatomical colon segment associated with the image, a transit pattern of the CE device, CE device communication errors, an anatomical landmark in the plurality of images, or coverage of GIT tissue in the plurality of images. Such uses and other uses are contemplated to be within the scope of the present disclosure.

Although the present disclosure provides systems and methods for identifying images of polyps with a high degree of confidence, not all occurrences of polyps may require a follow-up procedure. In particular, the size of a polyp is important in determining whether a follow-up procedure is needed. If a polyp is large enough, such as at least 6 mm in size, clinicians generally would like to examine a polyp by a colonoscopy procedure. In accordance with aspects of the present disclosure, the systems and methods of the present disclosure can determine whether or not to recommend a colonoscopy or to recommend a follow-up procedure in a particular number of months or years. Such a determination can be performed by a computing system, such as the computing system of FIG. 3.

Figure 15:
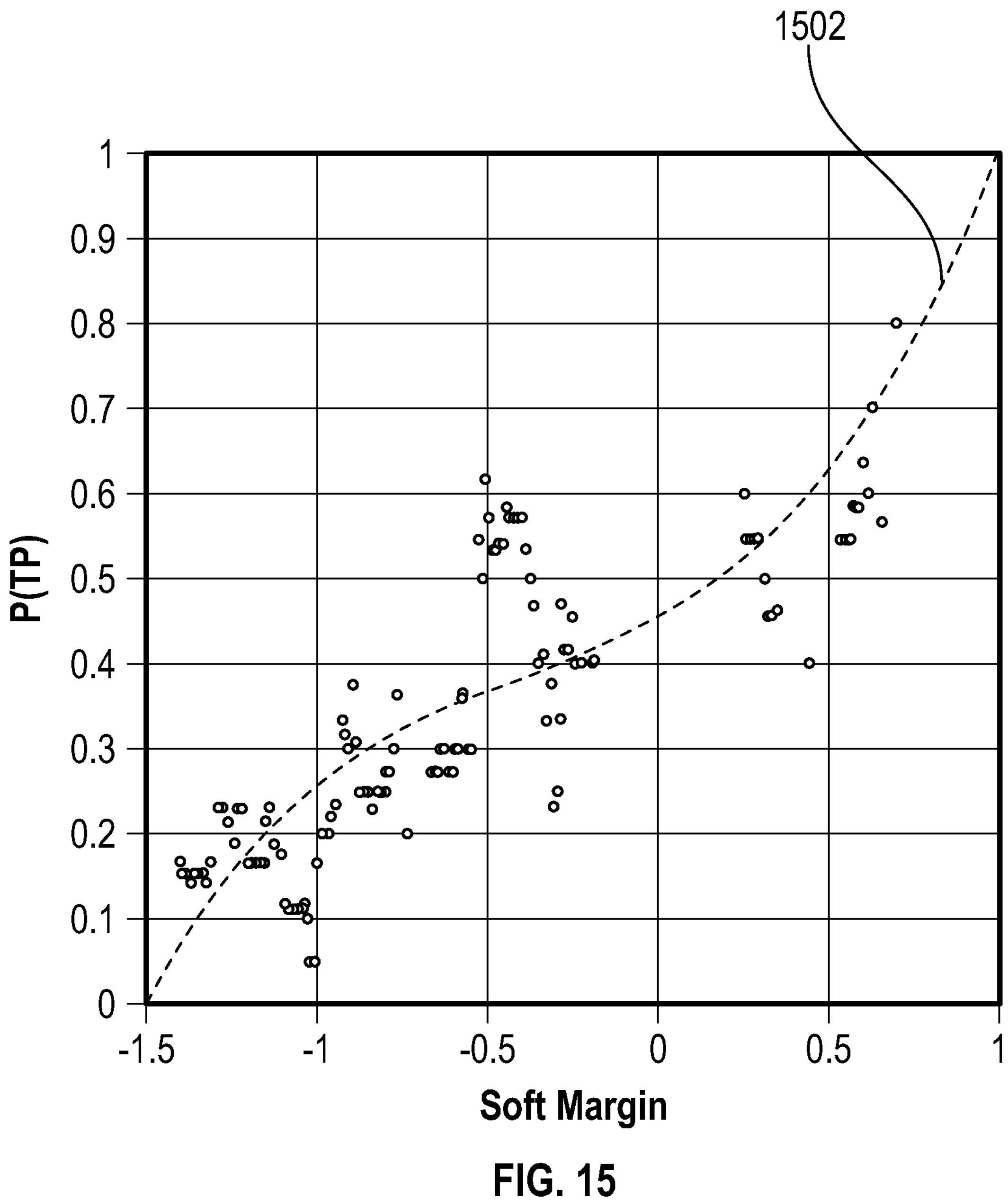
FIG. 15 is a graph for determining probability that an image contains a polyp based on soft margins, in accordance with aspects of the present disclosure.
Figure 16:
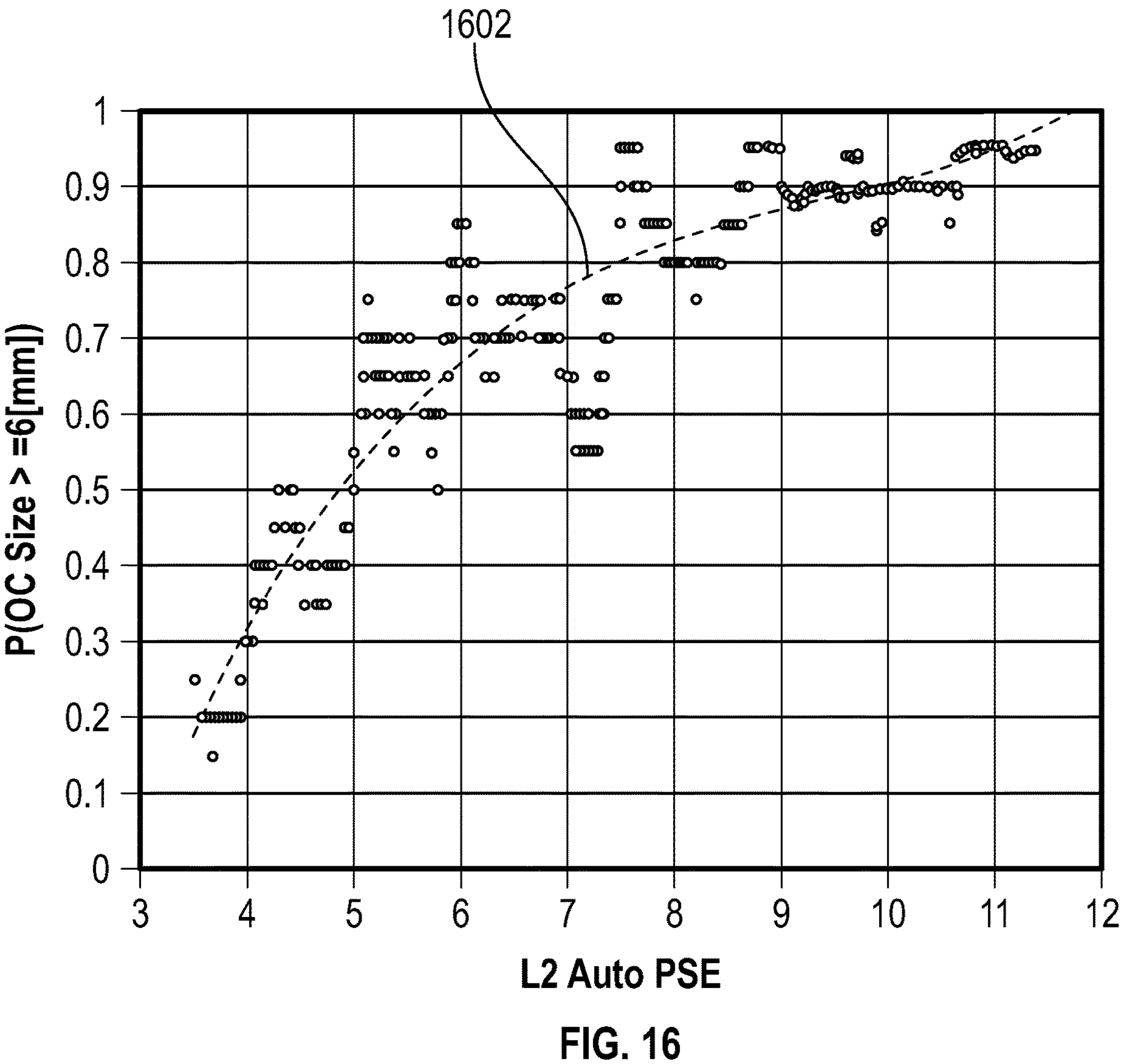
FIG. 16 is a graph for determining probability that an image contains a polyp at least 6 mm in size, in accordance with aspects of the present disclosure.

With reference to FIG. 15 and FIG. 16, the determination can be made based on a probability that there is at least one polyp that is 6 mm or larger in size. The determination uses the images identified by the processes of FIGS. 6, 8, and 9, which may be seed images designated by a positive filter as containing a polyp (block 630) or seed images which have a sufficiently high classification score or probability of containing a polyp (block 640, 650). Assuming there are n such images, $P_i$(TP & Size ≥6 [mm]) denotes the probability that image i includes a polyp and that the polyp is at least 6 mm in size. This probability includes two elements—whether the image includes a polyp, and whether a polyp is at least 6 mm in size. Assuming these two elements are independent, the probability can be expressed as:

$$P_i(TP\&\text{Size} \geq 6\ [\text{mm}]) = P_i(TP)P_i(\text{Size} \geq 6\ [\text{mm}]).$$

$P_i$(TP) denotes the probability that image i includes a polyp. $P_i$(Size ≥6 [mm]) denotes the probability that in image i, a polyp has size 6 mm or larger. For determining whether to recommend a colonoscopy procedure, only one candidate image needs to have a sufficiently high probability of including a polyp that is at least 6 mm in size.

FIG. 15 shows a graph which can be used for determining $P_i$(TP). The x-axis represents a soft margin for a machine learning system, such as the machine learning system in block 640 of FIGS. 6, 8, and 9. As persons skilled in the art will understand, a soft margin may refer to the continuous output of a classifier (e.g., a classical machine learning algorithm) which is related to the distance between an example and a separating hyperplane/classification border of the classifier. A soft margin can indicate how sure a machine learning system is that it has correctly classified an image as containing a polyp. The higher the absolute value of the soft margin, the farther from the classification border and the surer it is in its decision. By accessing the soft margins associated with a labeled training set, the graph of FIG. 15 can be empirically derived.

As an example, the x-axis of FIG. 15 can be divided into intervals of 0.1 or intervals of another size. For each soft margin interval, the number of training inputs corresponding to presence of a polyp and having a soft margin within that interval can be counted, and the number of training inputs corresponding to absence of a polyp and having a soft margin within that interval can be counted. The two counts can be used to empirically calculate the percentage of inputs which have a polyp and which have a soft margin within that interval. The percentage can be used a surrogate for the probability that an input has a polyp if its soft margin falls within the interval. FIG. 15 shows an exemplary result of such calculations. The probabilities are fairly noisy because they are empirically determined. A regression analysis can be performed to fit a curve 1502 to the empirical probabilities to provide a smooth estimator 1502 for determining $P_i$(TP) based on soft margin. The embodiments described above with respect to FIG. 15 are exemplary, and other method are contemplated for determining $P_i$(TP).

FIG. 16 shows a graph which can be used for determining $P_i$(Size ≥6 [mm]). The x-axis represents a polyp size estimation determined for capsule endoscopy (CE) images. As described above, polyp size can be estimated in the manner described in U.S. patent application No. 63/075,782, or by other techniques which will be understood by persons skilled in the art. Each training CE image for which an actual polyp size is known (e.g., at least 6 mm or less than 6 mm) can be processed to determine its estimated polyp size. The x-axis can be divided into intervals of estimated polyp sizes, such as intervals of 0.1 mm or intervals of another size. Training inputs having estimated polyp sizes which fall into an interval can be counted. The counts in an interval can be used to calculate a percentage of training inputs having actual polyp sizes 6 mm or larger, for the interval, and the empirical percentage can be used as a surrogate for the probability that an input has a polyp 6 mm or larger, in that interval. FIG. 16 shows an exemplary result of such calculations. The probabilities are fairly noisy because they are empirically determined. A regression analysis can be performed to fit a curve 1602 to the empirical probabilities to provide a smooth estimator 1602 for determining $P_i$(Size ≥6 [mm]) based on estimated polyp size. The embodiments described above with respect to FIG. 16 are exemplary, and other method are contemplated for determining $P_i$(Size ≥6 [mm]).

As mentioned above, the probability that a seed image has a polyp and that the polyp is at least 6 mm can be determined by $P_i$(TP)$P_i$(Size ≥6 [mm]). If any probability resulting from the computation is greater than a threshold value, such as 0.999 or another threshold value, the computation can determine that there is an image of a polyp that is 6 mm or greater and a colonoscopy can be recommended on this basis.

The embodiments described for using 6 mm as a polyp size boundary can be applied to another polyp size boundary, such as 5 mm or 7 mm or another polyp size boundary.

The embodiments described above and with respect to FIGS. 15 and 16 are exemplary. Other methods are contemplated for determining whether to recommend a colonoscopy. Such variations and others are contemplated to be within the scope of the present disclosure.

Referring to FIG. 17, there is shown an exemplary operation which may use the systems and methods of FIG. 15 and FIG. 16. At block 1710, the operation involves accessing a plurality of images of a gastrointestinal tract (GIT) captured by a capsule endoscopy device during a CE procedure. Each image of the plurality of images is suspected to include a polyp and is associated with a probability of containing the polyp. Additionally, the plurality of images includes seed images where each seed image is associated with one or more images of the plurality of images and the one or more images associated with each seed image are identified as suspected to include the same polyp as the associated seed image. At block 1720, the operation involves applying a polyp detection system on the seed images to identify seed images which include polyps. The polyp detection system is applied to each seed image of the seed images based on the one or more images associated with the seed image and the probabilities associated with the seed image and with the one or more associated images. At block 1730, the operation involves identifying images of the plurality of images which include polyps of a size equal to or higher than a predefined size. Each image of the plurality of images is further associated with an estimated size of the suspected polyp contained in the each image, and the polyp detection system is further applied to each seed image of the seed images based on the estimated polyp sizes associated with the seed image and with the one or more images associated with the seed image. At block 1740, the operation involves overruling exclusion of the procedure if the procedure is determined inadequate and excluded, when at least one seed image is identified to include a polyp of a size equal or higher that the predefined size or to include a predefined number of polyps of a size equal to or higher than the predefined size.

With regarding to block 1740, and as mentioned above, the technology for determining that a procedure is inadequate is disclosed in U.S. Provisional Application No. 63/075,778. Such tool provides an adequacy measure which indicates a measurement for effectiveness of the CE procedure in capturing a predefined event in the plurality of images, as explained above, and the adequacy measure for the procedure can be determined based on a characteristic measure, which can include a plurality of measures that indicate a probability of at least one of capturing or not capturing the predefined event.

With continuing reference to block 1740, the operation for overruling exclusion of the procedure can be based on heuristics, such as a threshold for polyp detection probability and/or optionally polyp size or a minimal number of images, among others. In various embodiments, the operation for overruling can be based on a probability per procedure of, for example, images including a polyp of at least a predefined size, based on the set of seed images (e.g., FIG. 15 and FIG. 16.). The operations of FIG. 17 are exemplary and variations are contemplated to be within the scope of the present disclosure.

Accordingly, the description above provided systems and methods for identifying images containing polyps with a high degree of confidence and provided various uses of such identified images. The aspects and embodiment described herein are exemplary and do not limit the scope of the present disclosure.

While several embodiments of the disclosure have been shown in the drawings, it is not intended that the disclosure be limited thereto, as it is intended that the disclosure be as broad in scope as the art will allow and that the specification be read likewise. Therefore, the above description should not be construed as limiting, but merely as exemplifications of particular embodiments. Those skilled in the art will envision other modifications within the scope and spirit of the claims appended hereto.

What is claimed is:

1. A method for identifying images including polyps, comprising:

accessing a plurality of images of a gastrointestinal tract (GIT) captured by a capsule endoscopy (CE) device during a CE procedure, wherein:

each image of the plurality of images is suspected to include a polyp and is associated with a probability of containing the polyp, and the plurality of images includes seed images, each seed image is associated with one or more images of the plurality of images, the one or more images associated with each seed image are identified as suspected to include the same polyp as the associated seed image; and applying a polyp detection system on the seed images to identify seed images which include polyps, wherein the polyp detection system is applied to each seed image of the seed images based on the one or more images associated with the respective seed image and the probabilities associated with the respective seed image and with the one or more associated images associated with the respective seed image; and identifying images of the plurality of images which include polyps of a size equal to or higher than a predefined size, wherein each image of the plurality of images is further associated with an estimated polyp size of the suspected polyp contained in the each image, and wherein the polyp detection system is further applied to each seed image of the seed images based on the estimated polyp sizes associated with the seed image and with the one or more images associated with the seed image, wherein the CE procedure is determined inadequate and excluded, and wherein at least one seed image is identified to include a polyp of a size equal to or higher than the predefined size or to include a predefined number of polyps of a size equal to or higher than the predefined size, the method further comprising overruling the exclusion of the CE procedure.

2. The method of claim 1, wherein the polyp detection system comprises at least one of: one or more positive filters, one or more negative filters, one or more classical machine learning systems, or a combination thereof.

3. The method of claim 2, wherein inputs to the one or more classical machine learning systems, the one or more positive filters or the one or more negative filters comprise at least one of: a seed image probability of containing a polyp, number of images associated with a seed image, number of images associated with a seed image having a probability of containing a polyp according to a predefined threshold, or a combination thereof.

4. The method of claim 1, further comprising providing an indication to a referring physician of the CE procedure to refer a subject of the CE procedure to a colonoscopy procedure based on the seed images identified to include polyps.

5. The method of claim 4, further comprising:

for each image of the plurality of images:

applying a classical machine learning system configured to provide the probability of the image containing the polyp, based on input features corresponding to the image, and accessing a soft margin of the classical machine learning system corresponding to the image; and determining, without human intervention, whether to recommend a colonoscopy based on the soft margins of the plurality of images.

6. The method of claim 5, further comprising accessing a mapping of soft margins to probabilities of an image containing a polyp, wherein the determining of whether to recommend a colonoscopy is further based on the mapping of soft margins to probabilities of an image containing a polyp.

7. The method of claim 5, further comprising:

for each image of the plurality of images, accessing an estimated polyp size for the image, the estimated polyp size generated based on the image; and accessing a mapping of estimated polyp sizes to probabilities of an actual polyp size being at least a predefined size, wherein the determining of whether to recommend a colonoscopy is further based on the estimated polyp sizes and the mapping of estimated polyp sizes to probabilities of an actual polyp size being at least a predefined size.

8. The method of claim 1, further comprising providing a therapeutic recommendation based on the seed images identified to include polyps.

9. The method of claim 1 further comprising displaying the seed images and indicating the seed images identified to include polyps.

10. A method for identifying images including polyps, comprising:

accessing a plurality of images of a gastrointestinal tract (GIT) captured by a capsule endoscopy device during a CE procedure, wherein:

each image of the plurality of images is suspected to include a polyp and is associated with a probability of containing the polyp, and the plurality of images includes seed images, each seed image is associated with one or more images of the plurality of images, the one or more images associated with each seed image are identified as suspected to include the same polyp as the associated seed image;

applying a polyp detection system on the seed images to identify seed images which include polyps, wherein the polyp detection system is applied to each seed image of the seed images based on the one or more images associated with the respective seed image and the probabilities associated with the respective seed image and with the one or more associated images associated with the respective seed image;

displaying at least the seed images to a user;

receiving user selections of images among the displayed images;

determining at least one unselected image, which was not selected by the user and which is among the seed images identified to include polyps; and presenting the at least one unselected image to the user.

11. The method of claim 10, wherein the images selected by the user are images selected to be included in a CE procedure report.

12. The method of claim 11, wherein the presenting of the at least one unselected image to the user is performed once a request to generate a report is received.

13. A computer-implemented method for recommending a colonoscopy, comprising:

accessing a plurality of images of a gastrointestinal tract (GIT) captured by a capsule endoscopy device, the plurality of images having a likelihood of containing a polyp;

for each image of the plurality of images:

applying a classical machine learning system configured to provide an indication, based on input features corresponding to the image, of whether the image contains a polyp or does not contain a polyp, and accessing a soft margin of the classical machine learning system corresponding to the image;

accessing a mapping of soft margins to probabilities of an image containing a polyp; and determining, without human intervention, whether to recommend a colonoscopy based on the soft margins of the plurality of images, wherein the determining of whether to recommend a colonoscopy is further based on the mapping of soft margins to probabilities of an image containing a polyp.

14. The computer-implemented method of claim 13, further comprising:

for each image of the plurality of images, accessing an estimated polyp size for the image, the estimated polyp size generated based on the image; and accessing a mapping of estimated polyp sizes to probabilities of an actual polyp size being at least a predefined size, wherein the determining of whether to recommend a colonoscopy is further based on the estimated polyp sizes and the mapping of estimated polyp sizes to probabilities of an actual polyp size being at least a predefined size.

15. A system for recommending a colonoscopy, comprising:

one or more processors; and at least one memory storing instructions which, when executed by the one or more processors, cause the system to:

access a plurality of images of a gastrointestinal tract (GIT) captured by a capsule endoscopy device, the plurality of images having a likelihood of containing a polyp;

for each image of the plurality of images:

apply a classical machine learning system configured to provide an indication, based on input features corresponding to the image, of whether the image contains a polyp or does not contain a polyp, and access a soft margin of the classical machine learning system corresponding to the image;

access a mapping of soft margins to probabilities of an image containing a polyp; and determine, without human intervention, whether to recommend a colonoscopy based on the soft margins of the plurality of images, wherein the determining of whether to recommend a colonoscopy is further based on the mapping of soft margins to probabilities of an image containing a polyp.

16. The system of claim 15, wherein the instructions, when executed by the one or more processors, further cause the system to:

for each image of the plurality of images, access an estimated polyp size for the image, the estimated polyp size generated based on the image; and access a mapping of estimated polyp sizes to probabilities of an actual polyp size being at least a predefined size, wherein the determining of whether to recommend a colonoscopy is further based on the estimated polyp sizes and the mapping of estimated polyp sizes to probabilities of an actual polyp size being at least a predefined size.

* * * * *